US009334253B2

United States Patent
Prakash et al.

(10) Patent No.: US 9,334,253 B2
(45) Date of Patent: May 10, 2016

(54) DIRECT TRIFLUOROMETHYLATIONS USING TRIFLUOROMETHANE

(75) Inventors: G. K. Surya Prakash, Hacienda Heights, CA (US); Parag V. Jog, Arcadia, CA (US); Patrice. T. D Batamack, Culver City, CA (US); George Olah, Beverly Hills, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 14/113,482

(22) PCT Filed: Apr. 19, 2012

(86) PCT No.: PCT/US2012/034228
§ 371 (c)(1),
(2), (4) Date: Nov. 7, 2013

(87) PCT Pub. No.: WO2012/148772
PCT Pub. Date: Nov. 1, 2012

(65) Prior Publication Data
US 2014/0066640 A1    Mar. 6, 2014

Related U.S. Application Data

(60) Provisional application No. 61/480,092, filed on Apr. 28, 2011.

(51) Int. Cl.
| | |
|---|---|
| C07D 307/44 | (2006.01) |
| C07C 29/62 | (2006.01) |
| C07C 41/01 | (2006.01) |
| C07F 7/08 | (2006.01) |
| C07C 29/40 | (2006.01) |
| C07C 303/16 | (2006.01) |
| C07C 41/30 | (2006.01) |
| C07C 41/50 | (2006.01) |
| C07C 201/12 | (2006.01) |
| C07C 45/45 | (2006.01) |
| C07D 213/26 | (2006.01) |
| C07D 307/42 | (2006.01) |
| C07C 17/269 | (2006.01) |
| C07C 17/32 | (2006.01) |
| C07B 39/00 | (2006.01) |

(52) U.S. Cl.
CPC .............. *C07D 307/44* (2013.01); *C07B 39/00* (2013.01); *C07C 17/269* (2013.01); *C07C 17/32* (2013.01); *C07C 29/40* (2013.01); *C07C 29/62* (2013.01); *C07C 41/01* (2013.01); *C07C 41/30* (2013.01); *C07C 41/50* (2013.01); *C07C 45/455* (2013.01); *C07C 201/12* (2013.01); *C07C 303/16* (2013.01); *C07D 213/26* (2013.01); *C07D 307/42* (2013.01); *C07F 7/0818* (2013.01); *C07F 7/0896* (2013.01); *C07C 2103/24* (2013.01)

(58) Field of Classification Search
USPC ........... 549/497; 556/476, 488, 478; 568/812, 568/649, 808, 807
See application file for complete search history.

(56) References Cited

U.S. PATENT DOCUMENTS

| | | | |
|---|---|---|---|
| 5,446,218 | A | 8/1995 | Webster et al. |
| 6,203,721 | B1 | 3/2001 | Roques et al. |
| 6,355,849 | B1 | 3/2002 | Roques et al. |
| 2003/0153778 | A1 | 8/2003 | Prakash et al. |
| 2004/0230079 | A1 | 11/2004 | Prakash et al. |
| 2006/0052643 | A1 | 3/2006 | Prakash et al. |

FOREIGN PATENT DOCUMENTS

| | | |
|---|---|---|
| FR | WO 98/22435 A1 | 5/1998 |
| FR | 2 827 285 A1 | 1/2003 |

OTHER PUBLICATIONS

International Search Report and Written Opinion, Appl. No. PCT/US2012/034228, Jul. 17, 2012.
Barhdadi et al., "Coupling of fluoroform with aldehydes using an electrogenerated base," Chem. Commun, pp. 1251-1252 (1998).
Billard et al., "New Stable Reagents for the Nucleophilic Trifluoromethylation. 1. Trifluoromethylation of Carbonyl Compounds with N-Formylmorpholine Derivatives," Organic Letters, 2(14):2101-2103 (2000).
Billard et al., "Trifluoromethylation of Nonenolizable Carbonyl Compounds with a Stable Piperazino Hemiaminal of Trifluoroacetaldehyde," Eur. J. Org. Chem, 2001(8):1467-1471 (2001).
Cho et al., "The Palladium-Catalyzed Trifluoromethylation of Aryl Chlorides," Science, 328(5986):1679-1681 (2010).
Haszeldiene et al., "Perfluoroalkyl Derivatives of Sulphur. Part I. Trifluoromethanesulphonic Acid," Journal of the Chemical Society, 4228-4232, p. 4228 (1954).

(Continued)

*Primary Examiner* — Kristin Vajda
(74) *Attorney, Agent, or Firm* — Winston & Strawn LLP

(57) ABSTRACT

A direct trifluoromethylation method preferably using a trifluoromethane as a fluoro-methylating species. In particular, the present method is used for preparing a trifluoromethylated substrate by reacting a fluoromethylatable substrate with a trifluoromethylating agent in the presence of an alkoxide or metal salt of silazane under conditions sufficient to trifluoromethylate the substrate; wherein the fluoromethylatable substrate includes chlorosilanes, carbonyl compounds such as esters, aryl halides, aldehydes, ketones, chalcones, alkyl formates, alkyl halides, aryl halides, alkyl borates, carbon dioxide or sulfur.

21 Claims, 1 Drawing Sheet

(56) References Cited

OTHER PUBLICATIONS

Molander et al., "Improved Synthesis of Potassium (Trifluoromethyl)trifluoroborate [K(CF3BF3)]," Organometallics, 22(16):3313-3315 (2003) Abstract.
European Search Report, EP12776629,, dated Sep. 11, 2014.
Sylvie Large et al.: "Nucleophilic Trifluoromethylation of Carbonyl Compounds and Disulfides with Trifluoromethane and Silicon-Containing Bases", J. Org. Chem., 65 (2000) pp. 8848-8856.
G.K. Surya Prakash et al.: "Perfluoroalkylation with Organosilicon Reagents", Chem. Rev. 97 (1997) pp. 757-786.
T. Billard et al., New Stable Reagents for the Nucleophilic Trifluoromethylation. 1. Trifluoromethylation of Carbonyl Compounds with N-Formylmorpholine Derivatives, Organic Letters, vol. 2, No. 14, p. 2101-2103 (2000).
Benoit Folleas et al., Fluoroform: an Efficient Precursor for the Trifluoromethylation of Aldehydes, Tetrahedron, vol. 56, 275-283 (2000).
English Translation of JP Office Action mailed Dec. 1, 2015.

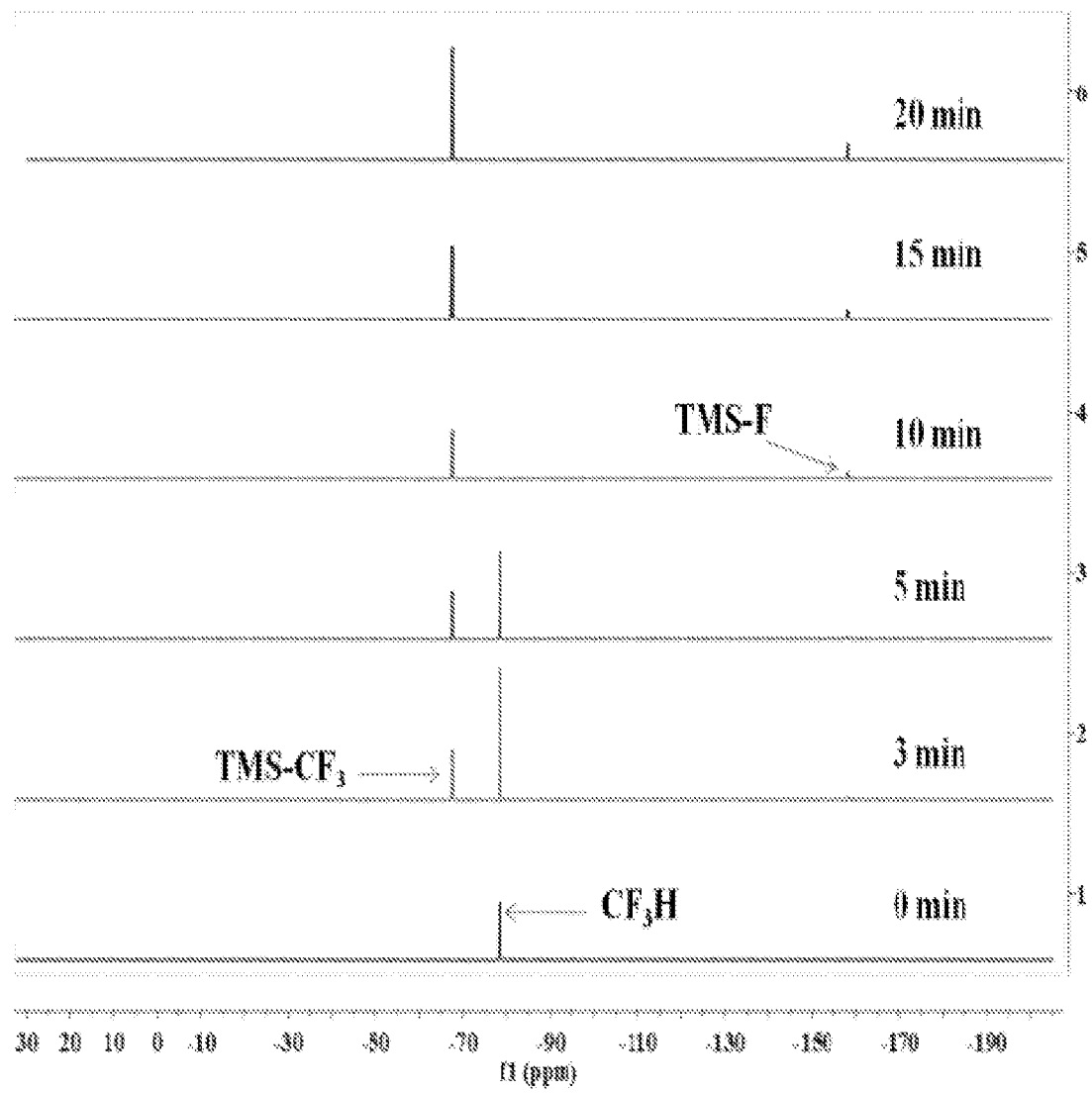

DIRECT TRIFLUOROMETHYLATIONS USING TRIFLUOROMETHANE

TECHNICAL FIELD

This invention relates to methods for direct trifluoromethylation of chlorosilanes, carbonyl compounds such as esters, aryl halides, aldehydes, ketones, chalcones, alkyl formates, alkyl halides, aryl halides, alkyl borates, carbon dioxide and sulfur using trifluoromethane ($CF_3H$) as a non-ozone depleting, trifluoromethylating agent.

BACKGROUND ART

Trifluoromethyl group plays a pivotal role in many industrial sectors such as pharmaceuticals, agrochemicals, dyes, polymers and material chemistry. It is well-known that introduction of fluorine in pharmaceutical targets increases the possibility of such compounds to act as "lead compounds" by almost tenfold (Taj, S. A. S. Chemical Industry Digest, 2008, 21, 92-98). Trifluoromethyl group increases the lipophilicity of biologically active compounds so that they can be absorbed by the body easily and can reach specific binding sites more effectively (Mueller, K., Faeh, C. and Diederich, F. Science 2007, 317, 1881-1886; Cho, E. J., Senecal, T. D., Kinzel, T., Zhang, Y., Watson, D. A. and Buchwald, S. L. Science 2010, 328, 1679-1681).

Consequently, the key challenge in the field is to develop safer, cheaper, environmentally friendly and more efficient trifluoromethylation methods. Nucleophilic trifluoromethylation is more attractive and well-studied to synthesize variety of trifluoromethylated building blocks. The most common reagent of choice for nucleophilic trifluoromethylation is trifluoromethyltrimethylsilane ($TMS-CF_3$), 1, also known as Ruppert-Prakash reagent (Ruppert, I., Schlich, K. and Volbach, W. Tetrahedron Lett., 1984, 25, 2195-2198; Ramaiah, P., Krishnamurti, R. and Prakash, G. K. S. Org. Synth., 1995, 72, 232-40). Trifluoromethyltrimethylsilane, 1, acts as a "trifluoromethide" equivalent in nucleophilic trifluoromethylation reactions (Prakash, G. K. S., Krishnamurti, R. and Olah, G. A. J. Am. Chem. Soc., 1989, 111, 393-395). Variety of methods have already been developed using this reagent to carry out nucleophilic trifluoromethylation of aldehydes, ketones, esters, imines, and many other electrophiles (both achiral and prochiral). (Prakash, G. K. S. and Yudin, A. K. Chem. Rev., 1997, 97, 757-786; Singh, R. P. and Shreeve, J. M. Tetrahedron, 2000, 56, 7613-7632; Prakash, G. K. S. and Hu, J. ACS Symp. Ser., 2005, 911, 16-56; Mizuta, S., Shibata, N., Sato, T., Fujimoto, H., Nakamura, S. and Toni, T. Synlett, 2006, 267-270; Kawai, H., Kusuda, A., Mizuta, S., Nakamura, S., Funahashi, Y., Masuda, H. and Shibata, N. J. Fluorine Chem., 2009, 130, 762-765). $TMS-CF_3$ (1) is commercially available and it is a very easy to handle liquid (bp=54-55° C.), both on industrial and laboratory scale.

Synthesis of $TMS-CF_3$ is also well studied and there are several methods, which are reported earlier (Ruppert, I., Schlich, K. and Volbach, W. Tetrahedron Lett., 1984, 25, 2195-2198; Ramaiah, P., Krishnamurti, R. and Prakash, G. K. S. Org. Synth., 1995, 72, 232-40; Beckers, H., Buerger, H., Bursch, P. and Ruppert, I. J. Organomet. Chem., 1986, 316, 41-50; Pawelke, G. J. Fluorine Chem., 1989, 42, 429-33; Deffieux, D., Bordeau, M., Biran, C. and Dunogues, J. Organometallics, 1994, 13, 2415-2422; Grobe, J. and Hegge, J. Synlett, 1995, 641-2; Prakash, G. K. S., Yudin, A. K., Deffieux, D. and Olah, G. A. Synlett, 1996, 151-3; Martynov, B. I. and Stepanov, A. A. J. Fluorine Chem., 1997, 85, 127-128; Prakash, G. K. S., Hu, J. and Olah, G. A. J. Org. Chem., 2003, 68, 4457-4463; Prakash, G. K. S., Hu, J. and Olah, G. A. 2004, US 2004/0230079 (A1), 33 pp; Prakash, G. K. S., Hu, J., Olah, G. A. and Wang, Y. 2005, US 2006/0052643 (A1), 28 pp). This reagent can be prepared by electrochemical procedures (Prakash, G. K. S., Deffieux, D., Yudin, A. K. and Olah, G. A. Synlett, 1994, 1057-8). In most of these methods the actual trifluoromethyl starting components include $CF_3I$, (Pawelke, G. J. Fluorine Chem., 1989, 42, 429-33) $CF_3Br$ (Ruppert, I., Schlich, K. and Volbach, W. Tetrahedron Lett., 1984, 25, 2195-2198; Ramaiah, P., Krishnamurti, R. and Prakash, G. K. S. Org. Synth., 1995, 72, 232-40), etc. Both $CF_3Br$ and $CF_3I$ are known ozone depleting gases and moreover their use is being regulated (Montreal protocol), which has resulted in slowing down the development of the synthesis of $TMS-CF_3$ on a large industrial scale. Intuitively, the simplest and rather atom economical source of the $CF_3$ moiety would be trifluoromethane ($CF_3H$). A multi-step synthesis of $TMS-CF_3$ (1) using trifluoromethane (via trifluoromethyl sulfide, sulfoxides and sulfones) and chlorosilanes using Mg mediated trifluoromethylation method has already been reported. (Prakash, G. K. S., Hu, J. and Olah, G. A. J. Org. Chem., 2003, 68, 4457-4463; Prakash, G. K. S., Hu, J. and Olah, G. A. 2004, US 2004/0230079 (A1), 33 pp). However, a direct trifluoromethylation of chlorosilanes with trifluoromethane to synthesize 1 and other higher trifluoromethylated silanes is still elusive. This is mainly due to the inherent and very well documented instability of trifluoromethyl anion even at very low temperatures. Trifluoromethyl anion ($CF_3^-$), due to its concentrated negative charge around the carbon atom, is known to decompose rapidly into fluoride ion ($F^-$) and an electron deficient singlet carbene, difluorocarbene, ($:CF_2$) (Prakash, G. K. S. and Mandal, M. J. Fluorine Chem., 2001, 112, 123-131; Large, S., Rogues, N. and Langlois, B. R. J. Org. Chem., 2000, 65, 8848-8856; Billard, T., Bruns, S. and Langlois, B. R. Org. Lett., 2000, 2, 2101-2103; Billard, T., Langlois, B. R. and Blond, G. Eur. J. Org. Chem., 2001, 1467-1471; Russell, J. and Rogues, N. Tetrahedron, 1998, 54, 13771-13782; Langlois, B. R. and Billard, T. Synthesis, 2003, 185-194).

Trifluoromethane, a by-product of the Teflon industry, is produced in large amounts on an industrial scale. Its efficient production has already been reported via fluorination of methane with hydrogen fluoride and chlorine. (Webster, J. L. and Lerou, J. J. 1995, U.S. Pat. No. 5,446,218 (A) 8 pp Cont-in-part of U.S. Ser. No. 51,917, abandoned). It is a non toxic, non ozone-depleting gas, but has a powerful greenhouse effect, which rules out its use as a refrigerant. Use of trifluoromethane gas in synthetic organic chemistry is a great challenge for a variety of reasons such as its low boiling point (bp=−83° C.), relatively high pKa (25-28), and low reactivity (being a relatively weak acid). On the other hand, this also can be considered as an interesting opportunity to develop synthetically useful methods by which one could convert an unused and accumulating byproduct, which is of environmental concern (because of green-house warming potential) into practical interests.

In 1991, Shono and others showed that an electrochemically generated base using 2-pyrrolidone can be used to deprotonate trifluoromethane, which generates in situ trifluoromethyl anion equivalent which then trifluoromethylates aldehydes and ketones (Shono, T., Ishifune, M., Okada, T. and Kashimura, S. J. Org. Chem., 1991, 56, 2-4). Troupel and others also showed that a strong base generated by cathodic reduction of iodobenzene can deprotonate trifluoromethane and consequently can then add to aldehydes (Barhdadi, R., Troupel, M. and Perichon, J. Chem. Commun., 1998, 1251-1252). Later on, two research groups have carried out extensive work where trifluoromethane is used as a source of trifluoromethyl anion. Normant et al. published their work on trifluoromethylation of aldehydes by deprotonation of trifluoromethane using Dimsyl-K (base generated from DMSO) in DMF (Folléas, B., Marek, I., Normant, J.-F. and Jalmes, L. S. Tetrahedron Lett., 1998, 39, 2973-2976). It was postulated that an adduct of $CF_3^-$ and DMF (hemiaminolate) acts as a reservoir of $CF_3^-$ anion and it was the true trifluoromethyl transfer intermediate. Subsequently, Langlois, Rogues and others reported trifluoromethylation of aldehydes, non-enolizable ketones and disulfides with an excess of $CF_3H$ and strong bases in DMF as a solvent, all of these are included herein as a reference (Large, S., Rogues, N. and Langlois, B. R. J. Org. Chem., 2000, 65, 8848-8856; Rogues, N., Russell, J., Langlois, B., Saint-Jalmes, L., Large, S. and et, a. 1998, WO 98/22435 (A1), 105 pp; Rogues, N. and Russell, J. 1997, U.S. Pat. No. 6,355,849 (B1), 32 pp; Langlois, B., Billard, T. and Garlyauskayte, R. 2003, FR 2827285 (A1), 22 pp). However, this method is limited to the use of dimethylformamide (or any amide containing reagent) to trap the trifluoromethyl anion in a hemi-aminolate and in absence of which the reaction does not seem to work well. In addition, in all of the reported reactions excess of trifluoromethane was used to achieve the desired trifluoromethylation reactions.

Based on the above, it is quite clear that there is a need to develop newer more direct trifluoromethylation methods, which use trifluoromethane as a direct trifluoromethylating source. These methods should be synthetically useful and versatile; practical, unrestricted (without any prerequisite solvent trap such as DMF) in terms of solvents used for the reaction and without the use of excess of trifluoromethane gas. Most beneficial would be a single step reaction between trifluoromethyl anion ($CF_3^-$), generated in situ from trifluoromethane and a given electrophile under suitable reaction conditions. Such methods would not only solve the environmental problem, which we face in future due to excess accumulation of this gas but would also provide practical synthetic applications.

SUMMARY OF THE INVENTION

The present invention relates to a method for preparing a trifluoromethylated substrate, which comprises reacting a fluoromethylatable substrate with a trifluoromethylating agent in the presence of a base under conditions sufficient to trifluoromethylate the substrate. The fluoromethylatable substrate generally comprises a compound selected from the group consisting of chlorosilanes, carbonyl compounds such as esters, aryl halides, aldehydes, ketones, chalcones, alkyl formates, alkyl halides, aryl halides, alkyl borates, carbon dioxide and sulfur. Also, the preferred trifluoromethylating agent is trifluoromethane.

The substrate typically comprises chlorotrimethylsilane, chlorotriethylsilane, chlorotriisopropylsilane, chloro(t-butyldimethyl)silane, chloro(tris(trimethylsilyl)) silane, dichlorodiethylsilane, benzaldehyde, p-anisaldehyde, 3-methylbenzaldehyde, 1-anthracenaldehyde, furan-2-carboxaldehyde, benzophenone, 4-methoxybenzophenone, 4-methylbenzophenone, 3-nitrobenzophenone, 4-fluorobenzophenone, chalcone, 4'-methoxychalcone, 4'-nitrochalcone, 4,4'-difluorochalcone, 4'-chlorochalcone, methyl benzoate, benzyl bromide, iodobenzene, 1-iodonaphthalene, 2-Iodoanisole, 3-nitroiodobenzene, 2-iodotoluene, 3-iodo-2-methoxynitrobenzene, 3-iodobenzotrifluoride, 2-iodopyridine, 3-iodopyridine, trimethoxyborate, tributylborate, elemental sulfur, methyl formate, or ethyl formate. When a ketone or carbonyl compound is used, it is preferably a non-enolizable compound.

The reaction is typically carried out in the presence of a solvent. For example, for trifluoromethylation of aryl halides the solvent is a polar aprotic solvent. Generally, however, the solvent is tetrahydrofuran (THF), diethyl ether, polyethers, hydrocarbon solvents (toluene, benzene, etc.), dimethyl ether, dimethoxymethane (Glyme), dimethylformamide (DMF), N-methylpyrrolidone (NMP), hexamethyl phosphoric triamide (HMPA), dimethyl sulfoxide (DMSO), preferably dimethylformamide (DMF).

The base comprises an alkoxide (polyalkoxide) or alkali metal salt of silazane (polysilazane) or a combination thereof. Also, the reaction conditions generally include a temperature of between about −90° C. to about 130° C. for a time between 30 minutes to 24 hours. A skilled artisan can determine the optimum conditions for any particular reactants by routine experimentation.

When the fluoromethylatable substrate comprises chlorosilanes, aldehydes, methyl benzoate, chalcones or non-enolizable ketones, the trifluoromethylating agent is trifluoromethane, and the base comprises an alkoxide (polyalkoxide) or alkali metal salt of silazane (polysilazane) or a combination thereof, the method further comprises adding the base to a mixture that includes the substrate and the trifluoromethylating agent to form a reaction mixture, stirring the reaction mixture at about −80° C. to −70° C. and warming the reaction mixture to about room temperature to trifluoromethylate the substrate. The reaction mixture is warmed to about room temperature for about 2 to 20 hours. Advantageoulsy, the reaction mixture is stirred vigorously either by magnetic stirring or mechanical stirring methods at all times.

When the fluoromethylatable substrate comprises aryl halides, the trifluoromethylating agent is trifluoromethane, and the base comprises an alkoxide (polyalkoxide) or alkali metal salt of silazane (polysilazane) or a combination thereof, the method further comprises adding the trifluoromethylating agent to a mixture of a copper halide, a heterocyclic ligand containing 1-10 heteroatoms, the solvent and the aryl halide followed by addition of the base to form a reaction mixture, stirring the reaction mixture at about 80 to 120° C. and cooling the reaction mixture to about room temperature to trifluoromethylate the substrate.

When the fluoromethylatable substrate comprises trialkylborates, these can be converted in situ to trifluoromethyltrifluoroborates.

When the fluoromethylatable substrate is elemental sulfur, it can be trifluoromethylated to a trifluoromethylated sulfur intermediate, which can then be oxidized in situ to form trifluoromethanesulfonic acid.

Preferred trifluoromethylated products include trifluoromethyl(trimethyl)silane, trifluoromethyl(triethyl)silane, trifluoromethyl(triisopropyl)silane, (trifluoromethyl)t-butyldimethylsilane, tris(trimethylsilyl)trifluoromethylsilane, diethylbis(trifluoromethyl)silane, 2,2,2-trifluoro-1-phenylethanol, 2,2,2-trifluoro-1-(4-methoxyphenyl)ethanol, 2,2,2-trifluoro-1-m-tolylethanol, 2,2,2-trifluoro-1-(furan-2-yl) ethanol, 1-(anthracen-9-yl)-2,2,2-trifluoroethanol, 2,2,2-trifluoro-1,1-diphenylethanol, 2,2,2-trifluoro-1-(4-methoxyphenyl)-1-phenylethanol, 2,2,2-trifluoro-1-phenyl-1-p-tolylethanol, 2,2,2-trifluoro-1-(3-nitrophenyl)-1-phenylethanol, 2,2,2-trifluoro-1-(4-fluorophenyl)-1-phenylethanol, (E)-1,1,1-trifluoro-2,4-diphenylbut-3-en-2-ol, (E)-1,1,1-trifluoro-2-(4-methoxyphenyl)-4-phenylbut-3-en-2-ol, (E)-1,1,1-trifluoro-2-(4-nitrophenyl)-4-phenylbut-3-en-2-ol, (E)-1,1,1-trifluoro-2,4-bis(4-fluorophenyl)but-3- en-2-ol, (E)-2-(4-chlorophenyl)-1,1,1-trifluoro-4-phenylbut-3-en-2-ol, 2,2,2-trifluoro-1-phenylethanone, 2,2,2-trifluoroethyl)benzene, (trifluoromethyl)benzene, 1-trifluoromethylnaphthalene, 1-methoxy-2-(trifluoromethyl)benzene, 1-nitro-3-(trifluoromethyl)benzene, 1-methyl-2-(trifluoromethyl)benzene, 2-methoxy-1-nitro-3-(trifluoromethyl)benzene, 1,3-bis(trifluoromethyl)benzene, 2-(trifluoromethyl)pyridine, 3-(trifluoromethyl)pyridine, potassium (Trifluoromethyl)trifluoroborate, trifluoromethanesulfonic acid, 1-methoxy-2,2,2-trifluoro ethanol, or 1-ethoxy-2,2,2-trifluoroethanol.

The invention also relates to the use of a trifluoromethylating agent for trifluoromethylating a fluoromethylatable substrate in the presence of a base under conditions sufficient to trifluoromethylate the substrate. As noted herein, the fluoromethylatable substrate generally comprises a compound selected from the group consisting of carbonyl compounds, chlorosilanes, esters, aryl halides, aldehydes, ketones, chalcones, alkyl halides, alkyl formates, alkyl borates, carbon dioxide, and sulfur, and the preferred trifluoromethylating agent is trifluoromethane.

BRIEF DESCRIPTION OF THE DRAWING FIGURES

The benefits and advantages of the present invention will become better known and understood upon a review of the following detailed description in combination with the appended drawing FIGURES, wherein:

FIG. 1 is a graph of the results of a low temperature $^{19}F$ NMR spectroscopic experiment.

DETAILED DESCRIPTION OF THE INVENTION

The purpose and advantages of the present invention will be set forth in and will become apparent from the description that follows, as well as will be learned by the practice of the invention. Additional advantages of the invention will be realized and attained by the reactions particularly pointed out in the written description and claims hereof, as well as from the appended FIGURES. To achieve these and other advantages and in accordance with the purpose of the invention, as embodied and described herein, the invention includes a convenient method of trifluoromethylation of a fluoromethylatable substrate or compound as noted as an example of a trifluoromethylating agent.

There has been a long standing interest, over the years, in improving synthetic methods for direct trifluoromethylation using trifluoromethane as a trifluoromethylating agent. New direct trifluoromethylation methods, using trifluoromethane ($CF_3H$) as a "trifluoromethyl" source, to trifluoromethylate chlorosilanes, carbonyl compounds such as esters, aryl halides, aldehydes, ketones, chalcones, alkyl formates, alkyl halides, aryl halides, alkyl borates, carbon dioxide and sulfur are disclosed herein. The details of these methods are discussed below.

The invention now provides a direct trifluoromethylation method preferably using a trifluoromethane as a fluoromethylating species and trifluoromethylating agent. A fluoromethylatable substrate or compound is the one that is capable of being trifluoromethylated in this fluoromethylation process. A "trifluoromethylating species" as the term used herein is for an agent capable of generating a trifluoromethylating species that is capable of forming a bond with the fluoromethylatable substrate.

In particular, the present method is used for preparing a trifluoromethylated substrate by reacting a fluoromethylatable substrate with a trifluoromethylating agent in the presence of an alkoxide, polyalkoxide or metal salt of silazane (polysilazane) under conditions sufficient to trifluoromethylate the substrate; wherein the fluoromethylatable substrate preferably comprises a compound selected from the group consisting of carbonyl compounds, chlorosilanes, aldehydes, ketones, chalcones, esters, alkyl halides, alkyl formates, aryl halides, alkyl borates and sulfur. The most preferred trifluoromethylating agent is trifluoromethane. Thus, in the description that follows, reference will be made to this preferred embodiment.

Specific electrophiles of the following nature are included in the invention:
1. $R_3$—Si—X, where R could be substituted or unsubstituted alkyl or aryl groups and X could be any halogen except fluorine (F), preferably chlorine (Cl).
2. Carbonyl compounds of the general formula R—CO—R' where R, R'=H, alkyl, aryl, O-alkyl and —CH=CH—Ar groups.
3. R—$CH_2$—X, where R could be substituted or unsubstituted alkyl or aryl groups and X could be any halogen except fluorine (F).
4. Ar—X, where Ar could be substituted or unsubstituted aryl ring and X could be any halogen except fluorine (F), preferably iodine (I).
5. $B(OR)_3$, where R could be substituted or unsubstituted alkyl or aryl groups.
6. Carbon dioxide.
7. Any source of sulfur including all of the oxidation states of sulfur such as S(II), S(IV), etc., with the most preferred source being elemental sulfur.

All the reactions are preferably performed under an inert atmosphere. Solvents used herein but are not limited to etheral solvents (for carbonyl and R—$CH_2$—X containing substrates), which contain at least one oxygen atom and in some cases hydrocarbons (containing only carbon and hydrogen) solvents with the absence of any heteroatoms. Polar solvents containing an amide functionality (R—CO—NR', R, R'=H, substituted or unsubstituted alkyl or aryl group) were used for aryl halides (Ar—X). Reactions can be performed in the temperature range of −78° C. to 130° C., preferably at −78° C. in the first step of the reaction in case of halosilanes, −40° C., for carbonyl and R—$CH_2$—X containing substrates and 130° C. for aryl halides. The preferred bases for this reaction comprises an alkoxide, polyalkoxide or alkali metal salt of silazane or a combination thereof and in particular are potassium salts of silazanes and polysilazanes, which contain nitrogen atoms (between 1-5, preferably 1) and silicon atoms (between 1-10, preferably 2) or alcohols with suitably branched alkyl group containing 1-20, preferably between 3-10 carbon atoms, with tertiary butyl being most preferred.

Base is dissolved in an appropriate solvent before the reaction and was present as slurry at the temperature at which the reaction is carried out. The reaction time could be between 1-20 hours, preferably 1-5 hours for halosilanes and 1-16 hours for carbonyl substrates and aryl halides.

In a preferred embodiment of the invention, the alkoxide, polyalkoxide or silazane(polysilazane) salt base is added to a mixture containing the substrate and trifluoromethylating agent. The reaction mixture is stirred at a first temperature, and is then warmed to a second temperature. Preferably the mixture is warmed to room temperature, around 20 to 25° C., for about 2 to 20 hours and preferably for about 5-6 hours.

1. Fluoromethylation of Silicon Containing Substrates

All the reaction conditions have been carefully optimized for each type of substrate. The parameters which needed to be optimized include equivalent of trifluoromethane, base and substrate. Optimization in the amount of solvent was also helpful (see Table 1 for the details of optimization conditions). Trifluoromethane gas is known to form hydrogen bonds (and hence dissolves readily) with many of the etheral solvents. Initial reactions were performed in dry tetrahydrofuran (THF). It is known that trifluoromethane forms a hydrogen bond with the oxygen of THF and hence has a good solubility in THF. Initial attempt to deprotonate trifluoromethane with a commercial solution of potassium hexamethyldisilazide (1M in THF) in the presence of trimethylsilyl chloride (TMS-Cl) at −40° C., yielded, along with many other peaks, a new fluorine peak in $^{19}F$ NMR at −67.3 ppm, which corresponded to the chemical shift of trifluoromethyl group in (trifluoromethyl)trimethylsilane (TMS-CF$_3$). Optimization of all the reaction conditions was carried out to maximize the yield of trifluoromethylation of chlorosilane and minimize any side reactions to form other by-products such as TMS-F (observed as a major side product in this reaction). The order of addition of all the reagents was optimized and the best optimized conditions in THF appeared to be the ones in which trifluoromethane was bubbled in dry THF at −78° C. followed by addition of neat TMS-Cl. This mixture was stirred at −78° C. for few minutes before the addition of KHMDS (1M in THF solution) drop wise slowly with very efficient stirring.

NMR ($^{19}F$) of a reaction mixture aliquot removed after 15 minutes of stirring at −78° C. showed desired trifluoromethylated product in good conversion (~44%, by $^1H$ NMR, internal standard, PhCF$_3$).

Presence of potassium ions in reaction mixture is important which is also evident from the previous observations in the literature (Billard, T., Langlois, Bernard R. and Blond, G. Eur. J. Org. Chem., 2001, 1467-1471). In addition to this, isolation and purification of TMS-CF$_3$ was extremely difficult when the reactions were performed in THF. Separation of TMS-CF$_3$ from the tristrimethylsilylamine, which was formed in the reaction as a side product, was difficult. Therefore, other solvents were examined for this transformation. While most etheral solvents work very well for the transformation, toluene (an aromatic hydrocarbon solvent) as a solvent seemed to work well with minimum formation of TMS-F under the optimized conditions. Reaction conditions were then optimized in toluene (an aromatic hydrocarbon solvent), and with the optimized procedure the percent conversion to TMS-CF$_3$ was greater than 90% and the pure product was isolated by distillation in overall 80% yield (See Table 1).

TABLE 1

Optimization of Reaction Conditions for the direct trifluoromethylation of trimethylsilyl chloride (TMS—Cl) using trifluoromethane (CF$_3$H)

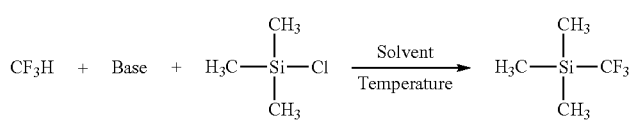

| Entry | CF$_3$H | Base (eq) | TMS—Cl (eq) | Temp. ° C. | Solvent | % Conversion to 1 by $^{19}F$ NMR |
|---|---|---|---|---|---|---|
| 1 | Excess | KHMDS (1 eq) | 1 | −78 | THF | 60 |
| 2 | Excess | KHMDS (1 eq) | 1 | −10 | THF | 15 |
| 3 | Excess | KHMDS (1 eq) | 1 | 25 | THF | 0 |
| 4 | Excess | tBuOK (1 eq) | 1 | −78 | THF | 0 |
| 5 | Excess | NaHMDS (1 eq) | 1 | −78 | THF | 0 |
| 6 | Excess | LiHMDS (1 eq) | 1 | −78 | THF | 0 |
| 7 | Excess | HKMDS (1 eq) | 1 | −60 to −78 | N-methylmorpholine | 0 |
| 8 | Excess | KHMDS (1 eq) | 1 | −78 | Diglyme | 0 |
| 9 | Excess | KHMDS (1 eq) | 1 | −78 | 1,2-Diethoxyethane | 0 |
| 10 | Excess | KHMDS (1 eq) | 1 | −50 to −78 | Dimethoxyethane | 75 |
| 11 | Excess | KHMDS (1 eq) | 1 | −50 | m-Anisole | 0 |
| 12 | Excess | KHMDS (1 eq) | 1 | −78 | Dibutylether | 0 |
| 13 | Excess | KHMDS (1 eq) | 1 | −78 | Dimethylether | 85 |
| 14 | Excess | t-BuOK (1 eq) | 1 | −78 | Dimethylether | 0 |
| 15 | Excess | KHMDS (1 eq) | 1 | −78 | Diethylether | 57 |
| 16 | 0.1M 0.2 (1 eq) | KHMDS (1 eq) | 1 | −78 | THF | 63 |
| 17 | 0.46M (1 eq) | KHMDS (1 eq) | 1 | −78 | THF | 63 |
| 18 | 0.5M (1 eq) | KHMDS (1 eq) | 1 | −78 | THF | 70 |
| 19 | 0.7M (1 eq) | KHMDS (1 eq) | 1 | −78 | THF | 66 |
| 20 | 1M (1 eq) | KHMDS (1 eq) | 1 | −78 | THF | 54 |
| 21 | 3.06M (1 eq) | KHMDS (1 eq) | 1 | −78 | THF | 55 |
| 22 | 0.5M (1 eq) | KHMDS (1 eq) | 1 | −78 | Toluene | 68 |
| 23 | 1 eq | KHMDS (1 eq) | 1.05 | −78 | Toluene | 97 (80)* |
| 24 | 1 eq | KHMDS (1 eq) | 1.05 | −78 | Diethyl ether | 96 |

*isolated yield (see experimental section)

With the current interest in palladium catalyzed trifluoromethylation reactions, other trifluoromethylsilanes [such as trifluoromethyltriethylsilane (TES-CF$_3$)] are becoming increasingly important source of the trifluoromethyl group because of their higher boiling points. The developed protocol was extended to synthesize other synthetically important trifluoromethylated silanes in good yields using ether as a solvent since the boiling points of most of the trifluoromethylated silanes were very close to the boiling point of toluene. Synthetic preparations of other trifluoromethylated silanes are very well established in the literature using trifluoromethyl halides, however, to the best of inventor's knowledge, the highest reported yield of (trifluoromethyl)triisopropylsilane is 9% whereas with the present methodology, the same compound can be obtained in 78% isolated yield (Table 2).

TABLE 2

Direct Trifluoromethylation of silyl chlorides using trifluoromethane ($CF_3H$)

| Entry | Silyl Chloride | Product | % yield | $^{19}F$ NMR in ppm |
|---|---|---|---|---|
| 1 | $H_3C$-Si($CH_3$)($CH_3$)-Cl | $H_3C$-Si($CH_3$)($CH_3$)-$CF_3$ | 80 | −67.3 |
| 2 | Et$_3$Si-Cl | Et$_3$Si-$CF_3$ | 71 | −61.3 |
| 3 | iPr$_3$Si-Cl | iPr$_3$Si-$CF_3$ | 78 | −55.4 |
| 4 | tBu-Si-Cl | tBu-Si-$CF_3$ | 42 | −61.8 |
| 5 | (Si)$_3$Si-Cl | (Si)$_3$Si-$CF_3$ | 68 | −41.4 |
| 6 | Et-Si(Cl)-Cl | Et-Si($CF_3$)-$CF_3$ | 44 | −60.2 |

In addition to monotrifluoromethylation reactions, bistrifluoromethylation of dichlorodimethylsilane and dichlorodiethylsilane using this methodology to obtain bis(trifluoromethyl)dimethylsilane and bis(trifluoromethyl)diethylsilane, previously inaccessible compounds, respectively, in good yields. However, isolation of bis(trifluoromethyl)dimethyl silane was difficult owing to its low boiling point (bp 30° C.). The same methodology can also be applied to synthesize phenyltris(trifluoromethyl)silane (from trichlorophenylsilane), however, other products (based on $^{19}F$ NMR) were observed in the reaction. Similarly, tetrakis(trifluoromethyl)silane (from silicon tetrachloride) was observed by $^{19}F$ NMR along with other fluorinated products (possibly, mono, bis and tris trifluoromethylated silanes). Due to complexity of the $^{19}F$ NMR, isolation and purification of these tris and tetrakis (trifluoromethylated) products was not pursued further.

2. Fluoromethylation of Carbon Electrophiles (Aldehydes, Non-Enolizable Ketones, Chalcones, Aromatic Esters, Benzyl Halides and Alkyl Formates)

Trifluoromethylation of aldehydes and non-enolizable ketones from fluoroform has already been reported. However, in all cases, excess of trifluoromethane was used and most of the reactions were carried out in presence of dimethylformamide (DMF), either as a solvent or in catalytic amounts. Encouraged by the results of trifluoromethylation of silanes in non polar solvents such as ether or toluene, trifluoromethylation of aldehydes and non-enolizable ketones was pursued under newly discovered reaction conditions. Trifluoromethylation of non-enolizable ketones went uneventfully and the corresponding trifluorometylated products were obtained in good yields using KHMDS to deprotonate trifluoromethane in using diethyl ether as a solvent. More importantly, trifluoromethane used was in equimolar amounts compared with the ketone and KHMDS (Table 3). In case of enolizable ketones, aldol condensation prevailed in ether, in THF and toluene the trifluoromethylated products were absent.

TABLE 3

Direct trifluoromethylation of aldehydes, non-enolizable ketones, chalcones, esters, alkyl halides and formates using trifluoromethane ($CF_3H$)

| Entry | Carbonyl Substrate | Product | % yield | $^{19}F$ NMR |
|---|---|---|---|---|
| 1 | Ph-C(=O)-Ph | Ph-C(OH)($CF_3$)-Ph | 71 | −74.8 |

TABLE 3-continued

Direct trifluoromethylation of aldehydes, non-enolizable ketones, chalcones, esters, alkyl halides and formates using trifluoromethane (CF₃H)

| Entry | Carbonyl Substrate | Product | % yield | $^{19}$F NMR |
|---|---|---|---|---|
| 2 | 4-methylphenyl phenyl ketone | 1-(4-methoxyphenyl)-1-phenyl-2,2,2-trifluoroethanol | 54 | −75 |
| 3 | 4-methylphenyl phenyl ketone | 1-(4-methylphenyl)-1-phenyl-2,2,2-trifluoroethanol | 53 | −74.9 |
| 4 | 3-nitrophenyl phenyl ketone | 1-(3-nitrophenyl)-1-phenyl-2,2,2-trifluoroethanol | 78 | −74.9 |
| 5 | 4-fluorophenyl phenyl ketone | 1-(4-fluorophenyl)-1-phenyl-2,2,2-trifluoroethanol | 81 | −75 |
| 6 | benzaldehyde | 1-phenyl-2,2,2-trifluoroethanol | 49 | −77.4 |
| 7 | 3-methylbenzaldehyde | 1-(3-methylphenyl)-2,2,2-trifluoroethanol | 42 | −75.6 |
| 8 | 4-methoxybenzaldehyde | 1-(4-methoxyphenyl)-2,2,2-trifluoroethanol | 34 | −78.8 |
| 9 | furfural | 1-(furan-2-yl)-2,2,2-trifluoroethanol | 43 | −78.5 |
| 10 | anthracene-9-carbaldehyde | 1-(anthracen-9-yl)-2,2,2-trifluoroethanol | 51 | −74.5 |

TABLE 3-continued

Direct trifluoromethylation of aldehydes, non-enolizable ketones, chalcones, esters, alkyl halides and formates using trifluoromethane (CF$_3$H)

| Entry | Carbonyl Substrate | Product | % yield | $^{19}$F NMR |
|---|---|---|---|---|
| 11 | chalcone | trifluoromethyl carbinol | 67 | −79.0 |
| 12 | 4-methoxy chalcone | trifluoromethyl carbinol | 63 | −79.0 |
| 13 | 4-nitro chalcone | trifluoromethyl carbinol | 0 | — |
| 14 | 4,4′-difluoro chalcone | trifluoromethyl carbinol | 38 | −79.3 |
| 15 | 4-chloro chalcone | trifluoromethyl carbinol | 60 | −79.3 |
| 16 | methyl benzoate | trifluoroacetophenone | 30* | −71.8 |
| 17 | benzyl bromide | benzyl-CF$_3$ | 10* | −66.6 |
| 18 | methyl formate | F$_3$C-CH(OH)-OCH$_3$ | 20* | |
| 19 | ethyl formate | F$_3$C-CH(OH)-OEt | 20* | |

*% Conversion based on $^{19}$F NMR analysis

Not surprisingly, in case of aldehydes, when KHMDS was used as a base to deprotonate trifluoromethane in THF, none of the trifluoromethylated products were observed because of competitive Cannizaro reaction between two aldehydes molecules under the reaction conditions employed. However, when the reaction was carried out in dry THF (in complete absence of DMF) and with t-BuOK instead of KHMDS, trifluoromethylation of aromatic aldehydes was achieved, albeit in low yields, even with the use of one equivalent of trifluoromethane.

Mechanistically, the reaction to produce TMS-CF$_3$ seem to proceed by deprotonation of trifluoromethane with potassium hexamethyldisilazide to generate trifluoromethyl anion, which immediately forms a pentacoordinated silicon species (A) with TMS-Cl which eventually looses chloride ion and generates trifluoromethyl trimethylsilane (Scheme 1).

Scheme 1:

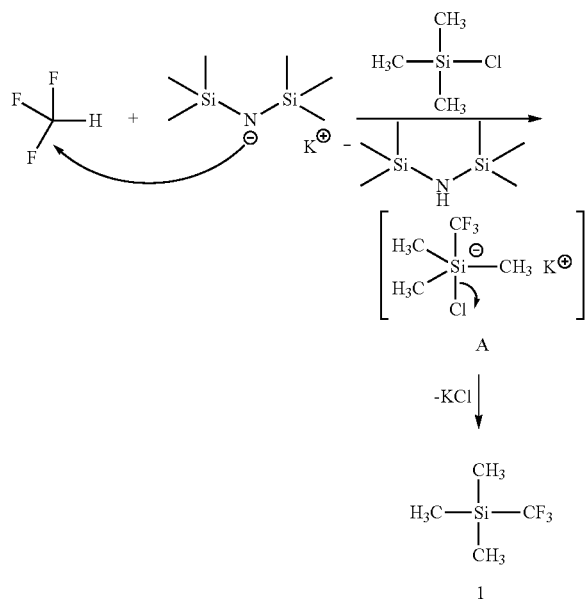

In order to ascertain whether this mechanism is viable and if species A can be observed spectroscopically, a low temperature experiment was performed. At −78° C., CF$_3$H was bubbled into a solution of toluene-d$_8$ and its $^{19}$F NMR spectra were recorded. To this NMR tube, a solution of potassium hexamethyldisilazide and TMS-Cl (which was made previously by mixing the two reagents in toluene at −78° C.) was added. Immediately, $^{19}$F NMR spectrum of this reaction mixture was recorded and collection of $^{19}$F NMR was continued for 20 minutes (at the interval of 5 minutes) and then the temperature of the NMR probe was gradually increased from −78° C. to Room Temperature (RT) over a period of 45 mins. The first spectrum recorded soon after the addition of base and TMSCl mixture showed presence of the product peak (TMS-CF$_3$) in addition to the unreacted CF$_3$H doublet in $^{19}$F NMR (FIG. 1). None of the substantial additional peaks in $^{19}$F NMR, besides a peak near 156 ppm which corresponds to TMS-F (a side product in this reaction) were observed. However, a small peak at −83 ppm was observed in all cases but unfortunately at this point its identity is not known. However, this experiment shows that the rate of formation of TMS-CF$_3$ is very rapid, which could be explained by the well known affinity of CF$_3$ anion for the electropositive silicon center to form the pentacoordinated species such as A.

In the case of aldehydes and non-enolizable ketones, the mechanism of the direct trifluoromethylation using trifluoromethane would be different (Scheme 2). While it has been known earlier that the "free" trifluoromethyl anion (CF$_3^-$) is unstable even at very low temperatures, as mentioned above, trifluoromethylation of aldehydes (including formaldehyde) and non-enolizable ketones was achieved, directly from trifluoromethane after deprotonation without subsequent trapping/stabilization of trifluoromethyl anion (generated in situ) with any other species.

Scheme 2:

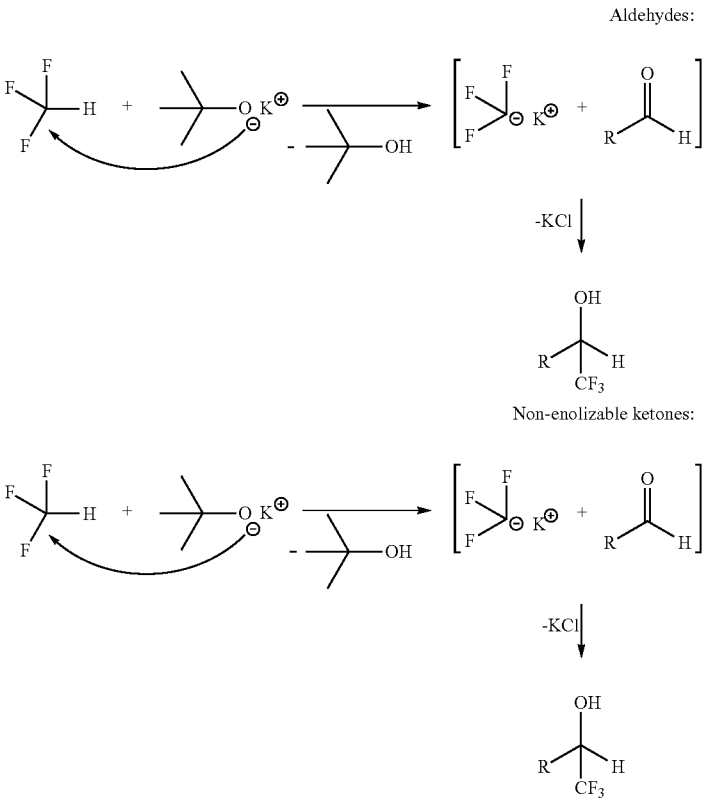

This methodology was extended to other electrophilic substrates such as chalcones, aromatic esters, benzyl halides, Cu salts, etc. Benzyl halides (chloride, bromide and iodide) showed only 10% conversion (by $^{19}$F NMR analysis) to the corresponding trifluoromethylated products and major product observed by NMR was the formation of benzyl fluoride. Aromatic esters also gave corresponding trifluoromethylated ketones in 30% conversion (by $^{19}$F NMR analysis). Similarly, trifluoromethylation of both ethyl formate and methyl formate gave trifluoroacetaldehyde ethyl hemiacetal and trifluoroacetaldehyde methyl hemiacetal in about 20% conversion based on $^{19}$F NMR analysis.

3. Fluoromethylation of Aromatic Halides

Trifluoromethylation of aromatic halides using copper salts have already been reported (Kobayashi, Y. and Kumadaki, I. Tetrahedron Lett., 1969, 4095-6; McLoughlin, V. C. R. and Thrower, J. Tetrahedron, 1969, 25, 5921-40; Kobayashi, Y., Yamamoto, K. and Kumadaki, I. Tetrahedron Lett., 1979, 4071-2; Matsui, K., Tobita, E., Ando, M. and Kondo, K. Chem. Lett., 1981, 1719-20; Umemoto, T. and Ando, A. Bull. Chem. Soc. Jpn., 1986, 59, 447-52; Carr, G. E., Chambers, R. D., Holmes, T. F. and Parker, D. G. J. Chem. Soc., Perkin Trans. 1, 1988, 921-6; Clark, J. H., McClinton, M. A. and Blade, R. J. J. Chem. Soc., Chem. Commun., 1988, 638-9; Chen, Q. and Wu, S. J. Chem. Soc., Chem. Commun., 1989, 705-6; Willert-Porada, M. A., Burton, D. J. and Baenziger, N. C. J. Chem. Soc., Chem. Commun., 1989, 1633-4; Su, D., Duan, J. and Chen, Q. Tetrahedron Lett., 1991, 32, 7689-90; Paratian, J. M., Sibille, S. and Perichon, J. J. Chem. Soc., Chem. Commun., 1992, 53-4; Chen, Q. and Duan, J. J. Chem. Soc., Chem. Commun., 1993, 1389-91; Heaton, C. A., Miller, A. K. and Powell, R. L. J. Fluorine Chem., 2001, 107, 1-3; Cottet, F. and Schlosser, M. Eur. J. Org. Chem., 2002, 327-330; Xiao, J.-C., Ye, C. and Shreeve, J. n. M. Org. Lett., 2005, 7, 1963-1965; Dubinina, G. G., Furutachi, H. and Vicic, D. A. J. Am. Chem. Soc., 2008, 130, 8600-8601; Dubinina, G. G., Ogikubo, J. and Vicic, D. A. Organometallics, 2008, 27, 6233-6235; Oishi, M., Kondo, H. and Amii, H. Chem. Commun., 2009, 1909-1911; Sato, K., Tarui, A., Omote, M., Ando, A. and Kumadaki, I. Synthesis, 2010, 1865-1882; Lundgren, R. J. and Stradiotto, M. Angew. Chem., Int. Ed., 2010, 49, 9322-9324; Morimoto, H., Tsubogo, T., Litvinas, N. D. and Hartwig, J. F. Angew. Chem. Int. Ed., 2011, 50, 3793-3798). However, the reagents used as a source of trifluoromethyl group have been silyl trifluoromethyl reagents or trifluoromethyl halides. Direct trifluoromethylation of unsubstituted aromatic halides using trifluoromethane ($CF_3H$) has not been reported and hence it was pursued. Initially, reactions were carried out in DMF as a solvent. Optimization of the reaction conditions are reported in Table 3. For the convenience of handling the corresponding trifluoromethylated products, 1-iodonaphthalene was chosen as the starting aromatic halide instead of iodobenzene (naphthyl-$CF_3$, bp=215° C. vs Ph-$CF_3$ bp=103° C.).

As evident from Table 4, direct trifluoromethylation of aromatic iodide has been achieved using trifluoromethane as a trifluoromethyl source in moderate yields (~50%). Unfortunately, in the presence of 1,10-phenanthroline as a ligand, we did not observe any "$CuCF_3$" species in the $^{19}$F NMR of the reaction mixture at room temperature or even at low (−10° C.) or high (100° C.) temperatures. However, in absence of 1,10-phenanthroline and in presence of an additive, a relatively stable $CuCF_3$ species was observed in $^{19}$F NMR. Reactions can be carried out in the presence or in absence of the ligand, however reactions which do not use any ligand gave better yields of the corresponding trifluoromethylated arenes. Additives could be any acid component (such as HF) or even crown ethers, which can coordinate potassium ions in the reaction mixture and avoid decomposition of $CuCF_3$ species via Cu=$CF_2$ carbenoid intermediates. Mechanistically, formation of hemiaminal of DMF (as a reactive species, when reaction was carried out in DMF) can be ruled out as a "$CF_3$" trapping species because HMPA (hexamethylphosphoric triamide), which cannot act as a trapping species also yielded 50% of the desired product under the identical reaction conditions (compare entries 3 vs 26, Table 2). Using the methodology described above, a variety of aryl halides have been trifluoromethylated directly using trifluoromethane as a trifluoromethylating reagent and the results obtained are summarized in Table 5.

TABLE 4

Optimization of Reaction Conditions for the direct trifluoromethylation of Aryl halides (Ar—X) using trifluoromethane ($CF_3H$).

$$Ar-X \; (A) + CF_3H \; (B) + CuX \; (C) + \text{1,10-Phenanthroline OR any additive} \; (D) \xrightarrow[\text{Solvent}]{\text{Base (E) Temperature Time}} Ar-CF_3 \; (F)$$

X = I unless otherwise noted
X = Cl unless otherwise noted

| Entry | A Ar: 1-naphthyl, unless otherwise noted eq | B eq | C eq | D 1,10-Phen unless otherwise noted eq | E Base: t-BuOK, unless otherwise noted eq | Temp ° C. | Time in h | Solvent | % yield of Cu—$CF_3$ by $^{19}$F NMR | F % yield* by $^{19}$F NMR |
|---|---|---|---|---|---|---|---|---|---|---|
| 1 | 1 | 2 | 2 | 2 | 2 | 130 | 5 | DMF | nd | 41 |
| 2 | 1 | 2 | 2, X = I | 2 | 2 | 130 | 16 | DMF | nd | 20 |
| 3 | 1 | 2 | 2 | 2 | 2 | 100 | 5 | DMF | nd | 50 |
| 4 | 1 | 2 | 2 | 2 | 2 | 100 | 16 | DMF | nd | 39 |
| 5 | 1 | 2 | 2 | 2 | 2 | 100 | 5 | DMF | nd | 45 |
| 6 | 1 | 2 | 4 | 4 | 2 | 100 | 5 | DMF | nd | 48 |
| 7 | 1 (Ph—I) | 2 | 2 | 2 | 2 | 100 | 5 | DMF | nd | 42 |

TABLE 4-continued

Optimization of Reaction Conditions for the direct trifluoromethylation of Aryl halides (Ar—X) using trifluoromethane (CF$_3$H).

$$\text{Ar—X} + \text{CF}_3\text{H} + \text{CuX} + \text{1,10-Phenanthroline OR any additive} \xrightarrow[\text{Solvent}]{\substack{\text{Base (E)} \\ \text{Temperature} \\ \text{Time}}} \text{Ar—CF}_3$$

A: X = I unless otherwise noted
B
C: X = Cl unless otherwise noted
D
F

| Entry | A Ar: 1-naphthyl, unless otherwise noted eq | B eq | C eq | D 1,10-Phen unless otherwise noted eq | E Base: t-BuOK, unless otherwise noted eq | Temp °C. | Time in h | Solvent | % yield of Cu—CF$_3$ by $^{19}$F NMR | F % yield* by $^{19}$F NMR |
|---|---|---|---|---|---|---|---|---|---|---|
| 8 | 1 | 2 | 2 C = copper (II) formate | 2 | 2 | 100 | 5 | DMF | nd | 0 |
| 9 | 1 | 2 | 2, x = acetate | 2 | 2 | 100 | 5 | DMF | nd | 33 |
| 10 | 1 | 2 | 2, x = oxide | 2 | 2 | 100 | 5 | DMF | nd | 0 |
| 11 | 1 | 2 | 2, C = "Cu powder" | 2 | 2 | 100 | 5 | DMF | nd | 0 |
| 12 | 1 | 2 | 2, x = cyanide | 2 | 2 | 100 | 5 | DMF | nd | 10 |
| 13 | 1 | 2 | 2 | 2 | 2 | 100 | 5 | DMF | nd | 50 |
| 14 | 1 (2-iodopyridine) | 2 | 2 | 2 | 2 | 100 | 5 | DMF | nd | 27 |
| 15 | 1 | 2 | 2 | 2 | 2 | 100 | 5 | THF | nd | 0 |
| 16 | 1 | 2 | 2 | 2 | 2 | 100 | 5 | Dimethoxyethane | nd | 0 |
| 17 | 1 (x = Cl) | 2 | 2 | 2 | 2 | 100 | 5 | DMF | nd | 10 |
| 18 | 1 | 2 | 2 | 2 | 2 | 100 | 5 | N-methylpyrrolidone (NMP) | nd | 20 |
| 19 | 1 | 2 | 2 | 2 | 1.2 (KHMDS) | 100 | 5 | DMF | nd | 0 |
| 20 | 1 | 2 | 2 | 2 | 1.5 (LDA) | 100 | 5 | DMF | nd | 0 |
| 21 | 1 | 2 | 2 | 2 | 1.5 (NaH) | 100 | 5 | DMF | nd | 0 |
| 22 | 1 | 2 | 2 | 2 | 5 | 100 | 5 | DMF | nd | 20 |
| 23 | 1 | 2 | 2 | 2 | 2 | RT | 24 | DMF | nd | 20 |
| 24 | 1 | 3 | 2 | 2 | 2 | RT | 24 | Toluene | nd | 0 |
| 25 | 1 | 3 | 3 | 3 | 3 | 100 | 5 | DMF | nd | 60 |
| 26 | 1 | 2 | 2 | 2 | 2 | 100 | 5 | HMPA | nd | 50 |
| 27 | 1.5 (Ph—I) | 3 | 1 | TREAT-HF (0.4 eq) | 2 | 50 | 24 | DMF | 87 | 35 | nd—% yield not determined
*yield determined using C$_6$F$_6$ as an internal reference

TABLE 5

Trifluoromethylation of aryl halides using trifluoromethane (CF$_3$H).

| Sr. No. | Aryl halide | Product | % yield* |
|---|---|---|---|
| 1 | 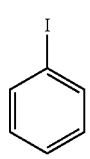 | 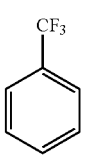 | 54 |
| 2 | 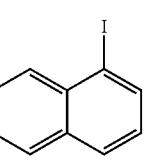 | 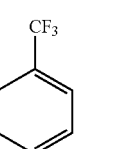 | 65 |

TABLE 5-continued

Trifluoromethylation of aryl halides using trifluoromethane (CF$_3$H).

| Sr. No. | Aryl halide | Product | % yield* |
|---|---|---|---|
| 3 | 2-iodoanisole | 2-(trifluoromethyl)anisole | 80 |
| 4 | 3-iodonitrobenzene | 3-(trifluoromethyl)nitrobenzene | 10 |
| 5 | 2-iodotoluene | 2-(trifluoromethyl)toluene | 48 |
| 6 | 2-iodo-3-methoxynitrobenzene | 2-(trifluoromethyl)-3-methoxynitrobenzene | 50 |
| 7 | 3-iodobenzotrifluoride | 1,3-bis(trifluoromethyl)benzene | 62 |
| 8 | 2-iodopyridine | 2-(trifluoromethyl)pyridine | 27 |
| 9 | 3-iodopyridine | 3-(trifluoromethyl)pyridine | 32 |

*% yield determined using C$_6$F$_6$ as an internal reference by $^{19}$F NMR

4. Fluoromethylation of trialkyl borates

Nucleophilic trifluoromethylation using organoboron reagents, specifically potassium trialkyl trifluoroborates, is becoming increasingly popular. The most common electrophiles include non-enolizable aldehydes, N-tosylimines (Levin, V. V., Dilman, A. D., Belyakov, P. A., Struchkova, M. I. and Tartakovsky, V. A. Tetrahedron Lett., 2011, 52, 281-284), aryl iodides (Knauber, T., Arikan, F., Roeschenthaler, G.-V. and Goossen, L. J. Chem.-Eur. J., 2011, 17, 2689-2697, 52689/1-52689/83) and more recently aryl boronates (Khan, B. A., Buba, A. E. and Goossen, L. J. Chem.-Eur. J., 2012, 18, 1577-1581).

Syntheses of the above-mentioned organoboron reagents (potassium trialkyltrifluoromethyl borates) is reported in the literature (Molander, G. A. and Hoag, B. P. Organometallics, 2003, 22, 3313-3315; Kolomeitsev, A. A., Kadyrov, A. A., Szczepkowska-Sztolcman, J., Milewska, M., Koroniak, H., Bissky, G., Barten, J. A. and Roeschenthaler, G.-V. Tetrahedron Lett., 2003, 44, 8273-8277). However, all of the reported methods use (trifluoromethyl)trimethylsilane (TMS-CF$_3$) as a source of trifluoromethyl group. A direct trifluoromethylation of trialkyl borates using trifluoromethane (CF$_3$H) is not reported. Based on our results with chlorosilanes, we pursued trifluoromethylation of trialkyl borates using trifluoromethane (CF$_3$H) as a direct source of trifluoromethyl anion. Trifluoromethylation of trialkyl borates (trimethyl borate and tri(n-butyl)borate) was achieved using trifluoromethane (1 equivalent) and KHMDS as a base in THF at −5° C. to RT. While potassium trifluoromethyltrimethyl borate (CF$_3$-B(OMe)$_3$K) was observed by $^{19}$F NMR in good yield (compared to internal standard C$_6$F$_6$), isolation of the salt in its pure form from the reaction mixture was difficult. This could possibly be due to the unreacted KHMDS being present in the reaction mixture which decomposed the desired product by further reacting with it. Hence we decided to fluorinate the potassium trifluoromethyltrimethyl borate using 48% HF (aq) in situ and isolate the corresponding potassium trifluoromethyltrifluoroborate salt. This transformation occurred smoothly and we were able to isolate both potassium trifluoromethyltrifluoroborate salts from both potassium trifluoromethyltrimethyl borate and potassium trifluoromethyltri-n-butyl borate (Scheme 3). This shows that trifluoromethylation of trialkyl borates can be achieved directly from trifluoromethane under basic conditions in THF, again in complete absence of DMF. This also proves that the "naked" trifluoromethyl anion formed after deprotonation of trifluoromethane can be used directly as a trifluoromethyl source (CF$_3$ source) without any stabilization of the anion as opposed to previous claims in the literature (Large, S., Rogues, N. and Langlois, B. R. J. Org. Chem., 2000, 65, 8848-8856; Billard, T., Bruns, S. and Langlois, B. R. Org. Lett., 2000, 2, 2101-2103; Billard, T., Langlois, B. R. and Blond, G. Eur. J. Org. Chem., 2001, 1467-1471; Russell, J. and Rogues, N. Tetrahedron, 1998, 54, 13771-13782; Langlois, B. R. and Billard, T. Synthesis, 2003, 185-194).

Scheme 3: Direct trifluoromethylation of trialkyl borates using trifluoromethane (CF$_3$H).

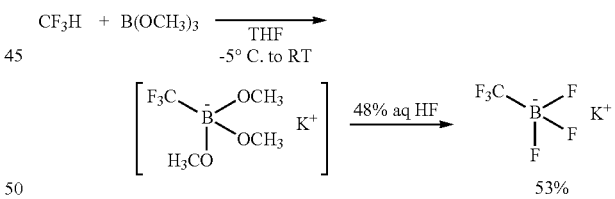

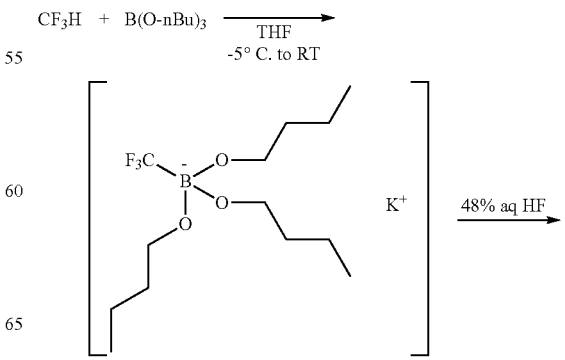

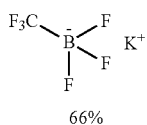

66%

5. Fluoromethylation of Elemental Sulfur

Direct trifluoromethylation of elemental sulfur using trifluoromethane and subsequent oxidation of the products obtained would be the most logical and direct synthesis of trifluoromethanesulfonic acid ($CF_3SO_3H$, trifluoromethanesulfonic acid). Incidentally, this approach has been attempted in the literature (Mukhopadhyay, S., Bell, A. T., Srinivas, R. V. and Smith, G. S. Org. Process Res. Dev., 2004, 8, 660-662) albeit with only limited success (1.5% yield based on $CF_3H$). This method uses $CF_3H$ in excess, and is carried out in DMF as a solvent, which is known to trap trifluoromethyl anion ($CF_3^-$).

Based on the success with direct trifluoromethylation using $CF_3H$, direct trifluoromethylation of elemental sulfur (one of the cheapest source of sulfur available) was achieved. After carefully screening a variety of reaction conditions such as form of sulfur (activated, sublimed, etc.), solvents (THF, Toluene, etc), temperatures (−80 to room temperature), reaction times (1-24 h), etc., a method was developed to directly trifluoromethylate elemental sulfur. The method does not use excess of $CF_3H$ and is not carried out in DMF. The intermediate products (trifluoromethylated sulfur species, $CF_3Sn$) obtained were subjected to complete oxidation using $H_2SO_4$/30% $H_2O_2$ to obtain trifluoromethanesulfonic acid ($CF_3SO_3H$) in 18% conversion (NMR analysis, Scheme 4). The reaction can be further optimized to achieve higher conversions.

Scheme 4: Direct trifluoromethylation of elemental sulfur using trifluoromethane ($CF_3H$).

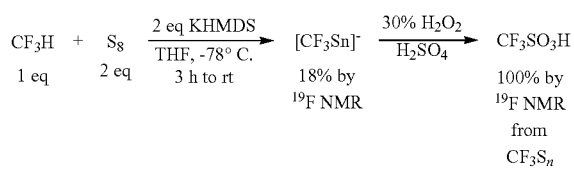

EXAMPLES

General: $CF_3H$ was used from Synquest Laboratories and was used as received. A gas mass flow controller from Aalborg (GFC-17) was used and was calibrated for $CF_3H$. Potassium hexamethyldisilazide (solid) was purchased from Aldrich and was stored under argon in a dry box. Commercially available solutions of potassium hexamethyldisilazide, both in THF and toluene, were purchased from Gelest Inc. and were used as received. All the chlorosilanes were purchased from Gelest Inc. and were used as received except for chlorotrimethylsilane (TMSCl), which was freshly distilled over calcium hydride just prior to the reaction. All other electrophiles were purchased from commercial sources such as Aldrich or other chemical suppliers and were used as received. All the reactions were carried out under argon atmosphere using dry solvents unless mentioned otherwise. $^1H$, $^{13}C$, $^{29}Si$, $^{11}B$ and $^{19}F$ NMR were recorded on 400 MHz NMR instrument with $CDCl_3$ (containing $CFCl_3$ for $^{19}F$, boric acid for $^{11}B$, TMS for $^{29}Si$ as standards for respective chemical shift values).

Example 1

Preparation of Trifluoromethyl(trimethyl)silane

To a 1000 ml three necked round bottom flask with a magnetic stirrer was added 376 ml of commercially available solution of potassium hexamethyldisilazide (0.6 M in toluene). This solution was then cooled to −85° C. using acetone/liquid nitrogen cooling bath for 20 minutes. A freshly distilled chlorotrimethylsilane (30 ml) was then added drop wise to the solution of hexamethyldisilazide in toluene. Resulting reaction mixture was stirred at −85° C. for 20 minutes. After 20 minutes, $CF_3H$ was bubbled in to the reaction mixture for 1 hour 38 minutes (15.8 g, bubbling rate 52.5 ml/min). After the bubbling of $CF_3H$ was over the resulting reaction mixture was stirred vigorously at −85° C. for 5 hours. After 5 hours, the resulting reaction mixture was slowly warmed to room temperature and then was stirred at room temperature for 2 hours. After 2 hours, air condenser along with head distillation apparatus with the thermometer was attached and reaction mixture was distilled. Fractions in the temperature range of 25-45° C. were collected as minor fractions and a major fraction was collected between 52-58° C. Major fraction contained mainly $TMSCF_3$ and (some) TMS-F mixture. This fraction was distilled again to obtain pure Trifluoromethyl(trimethyl)silane ($TMSCF_3$) 25.8 g, 80% yield. $^1H$ NMR (400 MHz): δ 0.27 (s); $^{13}C$ NMR (100.5 MHz): δ −5.18 (s, $CH_3$), 132.23 (q, $^1J_{C-F}$=322 Hz, $CF_3$). $^{19}F$ NMR (376.3 MHz): δ −67.3 (s); $^{29}Si$ NMR (79.5 MHz): δ 4.1 (q, $^2J_{Si-F}$=37.9 Hz, 1 Si).

Example 2

Preparation of Trifluoromethyl(triethyl)silane

To a 250 ml round bottom flask with magnetic stirrer, under argon was added 140 ml of diethyl ether. This reaction flask was cooled to −78° C. using dry ice/acetone bath and was stirred at that temperature for ten minutes. After ten minutes, $CF_3H$ was bubbled into this ether solution for 16 min 17 sec (2.5 g was added total at the rate of 52.5 ml/min to obtain 0.25 M solution in ether). After 10 minutes, chlorotriethylsilane (5.32 g) was added to the reaction mixture dropwise and the resulting reaction mixture was stirred at −78° C. for ten minutes. After ten minutes, a solution of potassium hexamethyldisilazide in ether (7.4 g in 52 ml, 0.625 M solution in ether) was added dropwise to the reaction mixture and the resulting yellowish reaction mixture was stirred at −78° C. for 2 hours and then was gradually warmed to room temperature and stirred at room temperature for 1 hour. Ether was removed under vacuo and the residue obtained was dissolved in pentane (150 ml). Organic layer (pentane) layer was washed with water once (1×30 ml) and was further washed with cold concentrated sulfuric acid (98%) (4×15 ml) to remove most of the siloxane and silanols formed in the reaction. Organic layer was then washed with water (5×50 ml) until pH of the water showed neutral and dried over sodium sulfate. Solvent (pentane) was removed under vacuo to obtain crude product which was distilled under vacuo to obtain pure (trifluoromethyl) triethylsilane 4.6 g, 71% yield. $^1H$ NMR (400 MHz): δ 0.79 (q, $^3J_{H-H}$=7.9 Hz, 6H), 1.04 (t, $^3J_{H-H}$=7.9 Hz, 9H), $^{13}C$ NMR (100.5 MHz): δ 0.86 (s, $CH_2$), 6.53 (s, $CH_3$), 132.24 (q, $^1J_{C-F}$=324 Hz, CF$_3$), $^{19}$F NMR (376.3 MHz): δ-61.3 (s), $^{29}$Si NMR (79.5 MHz): δ 7.7 (q, $^2J_{Si-F}$=32 Hz, 1 Si).

Example 3

Preparation of Trifluoromethyl(triisopropyl)silane

A similar procedure to the one reported in EXAMPLE 2 was followed except chlorotriisopropylsilane (5.02 g, 26 mmol, 1 eq) was used as the substrate to obtain (trifluoromethyl)triisopropylsilane 4.6 g, 78% yield, by 48° C./10 mm Hg. $^1$H NMR (400 MHz): δ 1.15 (d, $^3J_{H-H}$=7.4 Hz, 18H), 1.31 (m, 3H); $^{13}$C NMR (100.5 MHz): δ 9.47 (s, CH), 17.9 (s, CH$_3$), 132.5 (q, $^1J_{C-F}$=325 Hz, CF$_3$); $^{19}$F NMR (376.3 MHz): δ-55.4 (s); $^{29}$Si NMR (79.5 MHz): δ 5.99 (q, $^2J_{Si-F}$=27 Hz, 1 Si).

Example 4

Preparation of (Trifluoromethyl)t-butyldimethylsilane

A similar procedure to the one reported in EXAMPLE 2 was followed except chloro(t-butyldimethyl)silane (5.02 g, 33.3 mmol, 1 eq) was used as the substrate to obtain pure (trifluoromethyl)t-butyldimethylsilane 2.6 g, 42.3% yield. $^1$H NMR (400 MHz): δ 0.22 (s, 6H), 1.01 (s, 9H); $^{13}$C NMR (100.5 MHz): δ-8.73 (s, CH$_3$), 26.0 (s, C—CH$_3$), 132.0 (q, $^1J_{C-F}$=324 Hz, CF$_3$); $^{19}$F NMR (376.3 MHz): δ-61.8 (s); $^{29}$Si NMR (79.5 MHz): δ 8.33 (s, $^2J_{Si-F}$=33.1 Hz, 1 Si).

Example 5

Preparation of Tris(trimethylsilyl)trifluoromethylsilane

A similar procedure to the one reported in EXAMPLE 2 was followed except chloro(tris(trimethylsilyl))silane (5.25 g, 18.5 mmol, 1 eq) was used as the substrate to obtain pure tris(trimethylsilyl)trifluoromethylsilane 4.04 g, 68% yield. $^1$H NMR (400 MHz): δ 0.26 (s); $^{13}$C NMR (100.5 MHz): δ 0.49 (s, CH$_3$), 136.8 (q, $^1J_{C-F}$=328 Hz, CF$_3$); $^{19}$F NMR (376.3 MHz): δ-41.4 (s); $^{29}$Si NMR (79.5 MHz): δ-66.9 (q, $^2J_{Si-F}$=27 Hz, 1 Si), -12.5 (q, $^2J_{Si-F}$=4.4 Hz, 3 Si).

Example 6

Preparation of Diethyl bis(trifluoromethyl)silane

A similar procedure to the one reported in EXAMPLE 2 was followed except dichlorodiethylsilane (5.12 g, 32.5 mmol, 1 eq) was used as the substrate along with 2eq each of CF$_3$H and KHMDS to obtain pure diethyl bis(trifluoromethyl)silane 3.2 g, 44% yield. $^1$H NMR (400 MHz): δ 1.08 (m, CH$_2$), 1.16 (m, CH$_3$); $^{13}$C NMR (100.5 MHz): δ-1.10 (s, CH$_2$), 5.55 (s, CH$_3$), 128.6 (qq, $^1J_{C-F}$=319 Hz, 3.35 Hz, CF$_3$); $^{19}$F NMR (376.3 MHz): δ-60.2 (s); $^{29}$Si NMR (79.5 MHz): δ-2.43 (sept, $^2J_{Si-F}$=39.4 Hz, 1 Si).

Example 7

Preparation of 2,2,2-trifluoro-1-phenylethanol

To a 50 ml round bottom flask with stirrer under argon was added 15 ml of dry THF. This reaction flask was flushed with argon for 5 minutes before it was cooled to −40° C. using dry ice/acetone and was stirred at that temperature for ten minutes. After ten minutes, CF$_3$H was bubbled into this THF solution for 2 min 10 sec (0.3 g, 4.8 mmol was added total at the rate of 52.5 ml/min). This reaction mixture was allowed to stir for ten minutes. After 10 minutes, benzaldehyde (0.5 g, 4.7 mmol) was added to the reaction mixture dropwise and the resulting reaction mixture was stirred at −40° C. for ten minutes. After ten minutes, a solution of potassium tert-butoxide (4.7 ml, 4.7 mmol, 1 M solution in THF) was added dropwise to the reaction mixture and the resulting yellowish reaction mixture was stirred at −40° C. for 1 hour and then was gradually warmed to room temperature and stirred at room temperature for 10 hours. THF was removed under vacuo and the residue obtained was dissolved in ether and washed with water (25 ml×2) followed by brine (25 ml×2). Organic layer was dried over sodium sulfate and ether was removed under vacuo to obtain crude product. Column purification with ethyl acetate:hexane (1:9) gave pure product as colorless oil 0.41 g (49.4%). $^1$H NMR (400 MHz): δ 2.54 (d, 4.53 Hz, 1H, OH), 5.03 (m, 1H, C—H), 7.42 (m, 3H, Ar—H), 7.48 (m, 2H, Ar—H); $^{13}$C NMR (100.5 MHz): δ 67.2 (q, $^2J_{C-CF3}$=34.1 Hz, C—CF$_3$), 110.1, 110.7, 123.4 (q, $^1J_{C-F}$=282.4 Hz, CF$_3$), 143.6, 147.1; $^{19}$F NMR (376.3 MHz): δ-77.4 (d, $^3J_{F-H}$=6.42 Hz); MS (EI): m/z 176, 107 (M$^-$-CF$_3$), 79.

Example 8

Preparation of 2,2,2-trifluoro-1-(4-methoxyphenyl)ethanol

A similar procedure to the one reported in EXAMPLE 7 was followed except p-anisaldehyde (0.5 g, 3.67 mmol, 1 eq) was used as the substrate. Column purification with ethyl acetate:hexane (3:7) gave pure product as colorless oil 0.32 g (42.2%). $^1$H NMR (400 MHz): δ 2.61 (broad, 1H, OH), 3.82 (s, OCH$_3$), 4.96 (m, 1H, C—H), 6.93 (d, 8.7 Hz, 2H, Ar—H), 7.39 (m, 8.4 Hz, 2H, Ar—H); $^{13}$C NMR (100.5 MHz): δ 55.3 (s, OCH$_3$), 77.3 (q, $^2J_{C-CF3}$=32.1 Hz, C—CF$_3$), 114.0, 124.5 (q, $^1J_{C-F}$=282 Hz, CF$_3$), 125.7, 128.8, 160.4; $^{19}$F NMR (376.3 MHz): δ-75.6 (d, $^3J_{F-H}$=-6.4 Hz); MS (EI): 206 (m/z), 137 (M$^+$-CF$_3$), 109, 77.

Example 9

Preparation of 2,2,2-trifluoro-1-m-tolylethanol

A similar procedure to the one reported in EXAMPLE 7 was followed except 3-methylbenzaldehyde (0.5 g, 4.16 mmol, 1 eq) was used as the substrate. Column purification with ethyl acetate:hexane (2:8) gave pure product as colorless oil 0.27 g (34.1%). $^1$H NMR (400 MHz): δ 2.31 (s, Ar—CH$_3$), 2.45 (d, 4.6 Hz, 1H, OH), 4.91 (m, 1H, C—H), 7.20 (m, 4H, Ar—H); $^{13}$C NMR (100.5 MHz): δ 21.3 (s, Ar—CH$_3$), 72.7 (q, $^2J_{C-CF3}$=32 Hz, C—CF$_3$), 124.0 (q, $^1J_{C-F}$=282 Hz, CF$_3$), 124.5, 128.0, 128.5, 130.3, 133.9, 138.4; $^{19}$F NMR (376.3 MHz): δ-78.8 (d, $^3J_{F-H}$=6.7 Hz); MS (EI): 190 (m/z), 121 (M$^+$—CF$_3$), 91, 77.

Example 10

Preparation of 2,2,2-trifluoro-1-uran-2-yl)ethanol

A similar procedure to the one reported in EXAMPLE 7 was followed except furan-2-carbaldehyde (0.5 g, 5.2 mmol, 1 eq) was used as the substrate. Column purification with ethyl acetate:hexane (2:8) gave pure product as colorless oil 0.37 g (42.8%). $^1$H NMR (400 MHz): δ 2.60 (d, 7.3 Hz, 1H, OH), 5.06 (m, 1H, C—H), 6.43 (dd, 3.39, 1.87 Hz, 1H, Ar—H), 6.53 (d, 3.32 Hz, 1H, Ar—H), 7.48 (m, 1H, Ar—H); $^{13}$C NMR (100.5 MHz): δ 67.3 (q, $^2J_{C—CF_3}$=34 Hz, C—CF$_3$), 110.11, 110.76, 123.3 (q, $^1J_{C—F}$=282 Hz, CF$_3$), 143.6; $^{19}$F NMR (376.3 MHz): δ-78.5 (d, $^3J_{F—H}$=6.5 Hz); MS (EI): decomposed.

Example 11

Preparation of 1-(anthracen-9-yl)-2,2,2-trifluoroethanol

A similar procedure to the one reported in EXAMPLE 7 was followed except 1-anthracenaldehyde (0.5 g, 2.42 mmol, 1 eq) was used as the substrate. Column purification with ethyl acetate:hexane (1.5:8.5) gave pure product as colorless oil 0.34 g (50.7%). $^1$H NMR (400 MHz): δ 3.0 (br, 1H, OH), 6.68 (q, $^3J_{F—H}$=8.0 Hz, 1H, C—H), 7.51 (m, 2H, Ar—H) 7.59 (m, 2H, Ar—H), 8.05 (d, 8.4 Hz, 2H, Ar—H), 8.16 (br, 1H, Ar—H), 8.56 (m, 1H, Ar—H), 8.99 (br, 1H, Ar—H); $^{13}$C NMR (100.5 MHz): δ 70.1 (q, $^2J_{C—CF_3}$=33 Hz, C—CF$_3$), 120.0 (q, $^1J_{C—F}$=227 Hz, CF$_3$), 122.5, 123.8, 124.0, 125.0, 126.2, 127.0, 127.2, 129.2, 129.5, 130.8, 134.1; $^{19}$F NMR (376.3 MHz): δ-74.5 (d, $^3J_{F—H}$=8 Hz); MS (EI): 276 (m/z), 207 (M$^+$-CF$_3$), 178.

Example 12

Preparation of 2,2,2-trifluoro-1,1-diphenylethanol

To a 50 ml round bottom flask with stirrer under argon was added 10 ml of dry ether. This reaction flask was flushed with argon for 5 minutes before it was cooled to −50° C. using dry ice/acetone and was stirred at that temperature for ten minutes. After ten minutes, CF$_3$H was bubbled into this ether solution for 1 min 15 sec (0.19 g, 2.7 mmol was added total at the rate of 52.5 ml/min). This reaction mixture was allowed to stir for ten minutes. After 10 minutes, a solution of benzophenone (0.5 g, 2.7 mmol) in dry ether (5 ml) was added to the reaction mixture dropwise and the resulting reaction mixture was stirred at −40° C. for ten minutes. After ten minutes, a solution of potassium hexamethyldisilazide in ether (0.54 g in 5 ml, 2.7 mmol) was added dropwise to the reaction mixture and the resulting yellowish reaction mixture was stirred at −40° C. for 1 hour and then was gradually warmed to room temperature and stirred at room temperature for 10 hours. Reaction mixture was transferred to the separatory funnel and was washed with 5 ml of 1 N HCl, followed by saturated NaHCO$_3$ solution. Organic layer was washed with water (25 ml×2) followed by brine (25 ml×2) and then it was dried over sodium sulfate. Ether was removed under vacuo to obtain crude product. Column purification with pentane:acetone (9.5:0.5) gave pure product as colorless oil 0.49 g (71%). $^1$H NMR (400 MHz): δ 2.90 (s, 1H, OH), 7.37 (m, 6H, Ar—H), 7.5 (m, 4H, Ar—H); $^{13}$C NMR (100.5 MHz): δ 79.4 (q, $^2J_{C—CF_3}$=28 Hz, C—CF$_3$), 125.3 (q, $^1J_{C—F}$=286 Hz, CF$_3$), 127.4, 128.2, 128.6, 139.3; $^{19}$F NMR (376.3 MHz): δ-74.8 (s, CF$_3$); MS (EI): 252 (m/z), 183 (M$^+$-CF$_3$), 105, 77.

Example 13

Preparation of 2,2,2-trifluoro-1-(4-methoxyphenyl)-1-phenylethanol

A similar procedure to the one reported in EXAMPLE 12 was followed except 4-methoxybenzophenone (0.5 g, 2.4 mmol, 1 eq) was used as the substrate. Column purification with pentane:acetone (9:1) gave pure product as colorless oil 0.36 g (54%). $^1$H NMR (400 MHz): δ 2.87 (s, 1H, OH), 3.81 (s, 3H, Ar—CH$_3$), 6.88 (m, 2H, Ar—H), 7.37 (m, 5H, Ar—H), 7.50 (m, 2H, Ar—H); $^{13}$C NMR (100.5 MHz): δ 55.2, 79.1 (q, $^2J_{C—CF_3}$=28 Hz, C—CF$_3$), 113.5, 125.5 (q, $^1J_{C—F}$=286 Hz, CF$_3$), 127.3, 128.1, 128.5, 128.7, 131.5, 139.5, 159.5; $^{19}$F NMR (376.3 MHz): δ-75.0 (s, CF$_3$); MS (EI): 282 (m/z), 213 (M$^+$-CF$_3$), 135, 105, 77.

Example 14

Preparation of 2,2,2-trifluoro-1-phenyl-1-p-tolylethanol

A similar procedure to the one reported in EXAMPLE 12 was followed except 4-methylbenzophenone (0.5 g, 2.6 mmol, 1 eq) was used as the substrate. Column purification with pentane:acetone (9.5:0.5) gave pure product as colorless oil 0.36 g (53%). $^1$H NMR (400 MHz): δ 2.37 (s, 3H, Ar—CH$_3$), 2.87 (s, 1H, OH), 7.18 (m, 2H, Ar—H), 7.38 (m, 5H, Ar—H), 7.51 (m, 2H, Ar—H) $^{13}$C NMR (100.5 MHz): δ 21.0, 79.3 (q, $^2J_{C—CF_3}$=28 Hz, C—CF$_3$), 125.4 (q, $^1J_{C—F}$=286 Hz, CF$_3$), 127.2, 127.3, 128.1, 128.5, 128.9, 136.4, 138.5, 139.3; $^{19}$F NMR (376.3 MHz): δ-74.9 (s, CF$_3$); MS (EI): 266 (m/z), 197 (M$^+$-CF$_3$), 119, 105, 91.

Example 15

Preparation of 2,2,2-trifluoro-1-(3-nitrophenyl)-1-phenylethanol

A similar procedure to the one reported in EXAMPLE 12 was followed except 3-nitrobenzophenone (0.5 g, 2.2 mmol, 1 eq) was used as the substrate. Column purification with pentane:acetone (8.5:1.5) gave pure product as colorless oil 0.51 g (78%). $^1$H NMR (400 MHz): δ 3.16 (s, OH), 7.41 (m, 3H, Ar—H), 7.49 (m, 2H, Ar—H), 7.54 (m, 1H, Ar—H), 7.8 (m, 1H, Ar—H), 8.22 (m, 1H, Ar—H), 8.43 (m, 1H, Ar—H), $^{13}$C NMR (100.5 MHz): δ 79.0 (q, $^2J_{C—CF_3}$=29 Hz, C—CF$_3$), 122.6, 123.6, 124.9 (q, $^1J_{C—F}$=282 Hz, CF$_3$), 127.0, 128.8, 129.1, 129.3, 133.6, 138.4, 141.0, 148.0; $^{19}$F NMR (376.3 MHz): δ-74.9 (s, CF$_3$); MS (EI): 297 (m/z), 228 (M$^+$-CF$_3$), 150, 105, 77.

Example 16

Preparation of 2,2,2-trifluoro-1-(4-fluorophenyl)-1-phenylethanol

A similar procedure to the one reported in EXAMPLE 12 was followed except 4-fluorobenzophenone (0.5 g, 2.5 mmol, 1 eq) was used as the substrate. Column purification with pentane:acetone (9.5:0.5) gave pure product as colorless oil 0.55 g (81%). $^1$H NMR (400 MHz): δ 2.91 (s, 1H, OH), 7.05 (m, 2H, Ar—H), 7.38 (m, 3H, Ar—H), 7.48 (m, 4H, Ar—H); $^{13}$C NMR (100.5 MHz): δ 79.1 (q, $^2J_{C—CF_3}$=29 Hz, C—CF$_3$), 115.0, 115.2, 125.2 (q, $^1J_{C—F}$=286 Hz, CF$_3$), 127.2, 128.4, 128.8, 129.4, 129.5, 135.0, 139.2, 161.4, 163.9; $^{19}$F NMR (376.3 MHz): δ−75.0 (s, CF$_3$), −113.64 (m, Ar—F); MS (EI): 270 (m/z), 201 (M$^+$-CF$_3$), 123, 95, 77.

Example 17

Preparation of (E)-1,1,1-trifluoro-2,4-diphenylbut-3-en-2-ol

A similar procedure to the one reported in EXAMPLE 12 was followed except chalcone (0.2 g, 0.96 mmol, 1 eq) was used as the substrate. Column purification with pentane:ether (8:2) gave pure product as an oil 0.18 g (67%). $^1$H NMR (400 MHz): δ 7.67 (m, 2H), 7.38 (m, 8H), 6.92 (d, J=16.1 Hz, 1H), 6.76 (d, J=16.1 Hz, 1H), 2.75 (br, 1H); $^{13}$C NMR (100.5 MHz): δ 137.33, 135.45, 133.50, 128.79, 128.71, 128.62, 128.35, 126.89, 126.79, 126.42, 125.19 (J=286 Hz), 123.56, 120.72, 77.20 (J=29.1 Hz); $^{19}$F NMR (376.3 MHz): δ-79.03 (s, 3F).

Example 18

Preparation of (E)-1,1,1-trifluoro-2-(4-methoxyphenyl)-4-phenylbut-3-en-2-ol

A similar procedure to the one reported in EXAMPLE 12 was followed except 4'-methoxychalcone (0.2 g, 0.84 mmol, 1 eq) was used as the substrate. Column purification with pentane:ether (6:4) gave pure product as an oil 0.16 g (63%). $^1$H NMR (400 MHz): δ 7.67 (m, 2H), 7.39 (m, 5H), 6.90 (m, 2H), 6.81 (d, J=16.0 Hz, 1H), 6.59 (d, J=16.0 Hz, 1H), 3.82 (s, 3H), 2.84 (br, 1H); $^{13}$C NMR (100.5 MHz): δ 159.87, 137.52, 133.08, 128.68, 128.27, 128.17, 126.85, 125.5 (J=286 Hz), 124.15, 114.09, 77.20 (J=28.7 Hz), 77.00, 55.28; $^{19}$F NMR (376.3 MHz): δ-79.05 (s, 3F).

Example 19

Preparation of (E)-1,1,1-trifluoro-2,4-bis(4-fluorophenyl)but-3-en-2-ol

A similar procedure to the one reported in EXAMPLE 12 was followed except 4,4'-difluorochalcone (0.2 g, 0.81 mmol, 1 eq) was used as the substrate. Column purification with pentane:ether (8:2) gave pure product as an oil 0.10 g (38%). $^1$H NMR (400 MHz): δ 7.59-7.66 (m, 2H), 7.40 (dd, J=8.7, 5.3 Hz, 2H), 6.98-7.15 (m, 4H), 6.83 (d, J=16.1 Hz, 1H), 6.61 (d, J=16.1 Hz, 1H), 2.66 (br, 1H); $^{13}$C NMR (100.5 MHz): δ 164.18, 161.66, 133.01, 132.74, 131.43, 128.81, 128.62, 125.94, 115.88, 115.42, 77.00; $^{19}$F NMR (376.3 MHz): δ-79.35 (s, 3F), −112.91, −113.46.

Example 20

Preparation of ((E)-2-(4-chlorophenyl)-1,1,1-trifluoro-4-phenylbut-3-en-2-ol

A similar procedure to the one reported in EXAMPLE 12 was followed except 4'-chlorochalcone (0.2 g, 0.83 mmol, 1 eq) was used as the substrate. Column purification with pentane:ether (8:2) gave pure product as an oil 0.155 g (60%). $^1$H NMR (400 MHz): δ 7.58 (d, J=8.9 Hz, 2H), 7.38 (m, 8H), 6.86 (d, J=16.1 Hz, 1H), 6.69 (d, J=16.1 Hz, 1H), 2.66 (br, 1H); $^{13}$C NMR (100.5 MHz): δ 135.7, 135.2, 134.9, 134.1, 128.8, 128.7, 128.5, 128.4, 126.9, 126.0, 124.8 (J=286 Hz), 77.0 (J=29.1 Hz); $^{19}$F NMR (376.3 MHz): δ-79.3 (s, 3F).

Example 21

General Procedure for the Trifluoromethylation of Unsubstituted Aromatic Halides In a 10-15 mL vial with a magnetic stirrer, copper (I) chloride (0.3 g, 3.0 mmol, 1 eq) was added and the vial was sealed in the glove box under argon. To this vial, under argon 3 mL of dry DMF was added and the resulting reaction mixture was stirred at room temperature for 5 minutes. To this reaction mixture a solution of t-BuOK in DMF (0.68 g, 6.06 mmol, 2 eq) was added drop wise and the resulting reaction mixture was stirred at room temperature for 5 minutes. After 5 minutes, CF$_3$H was bubbled into this THF solution for 4 min 11 sec (0.636 g, 9.09 mmol was added total at the rate of 52.5 ml/min, 3 eq) and the resulting reaction mixture was stirred at room temperature for 10 minutes. After 10 minutes, a solution of triethylamine trihydrofluoride (TREAT HF) (0.195 g, 1.21 mmol, 198 μm) was added to the reaction mixture neat. To the same reaction mixture iodobenzene (0.927 g, 4.54 mmol, 1.5 eq) was added neat and the resulting reaction mixture was heated at 50° C. for 24 hours. The reaction mixture was cooled to room temperature and then hexafluorobenzene (C$_6$F$_6$) (0.166 eq) was added to the reaction mixture and it was stirred at room temperature for 10 mins. An aliquot of reaction mixture was taken out and its NMR ($^{19}$F) was recorded. NMR yields were determined by NMR integrations and are reported in Table 3.

General procedures for the trifluoromethylation of trialkyl borates

Example 22

Potassium (trifluoromethyl)trifluoroborate (K[CF$_3$—BF$_3$]) from Trimethoxyborate [B(OCH$_3$)$_3$]

In a 10-15 mL vial with magnetic stirrer under argon was added 10 ml of dry THF. The vial was cooled to 0 to −5° C. for 5 minutes. After ten minutes, CF$_3$H was bubbled into this THF solution for 4 min 26 sec (0.674 g, 9.62 mmol was added total at the rate of 52.5 ml/min). This reaction mixture was allowed to stir for ten minutes. After 10 minutes, trimethoxyborane (1 g, 9.62 mmol, 1.07 mL) was added to the reaction mixture neat. The resulting reaction mixture was stirred at 0° C. for 5 minutes. After 5 minutes, a solution of potassium hexamethyldisilazide (KHMDS) in THF (1.92 g, 9.62 mmol, 1 eq) was added to the reaction mixture drop wise and the resulting yellowish reaction mixture was stirred at 0° C. for 1-2 hrs and then the reaction mixture was allowed to warm to room temperature slowly overnight for 16 h. After 16 hours, 30 ml of water was added to the reaction mixture and the reaction mixture was stirred for 15 minutes. Reaction mixture was concentrated under vacuo to remove volatiles. Reaction mixture was further concentrated to half of its original volume under vacuo to remove water. Crude product obtained was transferred to a polyethylene (NALGENE®) bottle. This bottle was cooled in ice and then 48% aqueous solution of hydrogen fluoride (6 mL) was added to it. The resulting solution was stirred at ambient temperature for 12-14 hours. After that, a solution of potassium hydroxide (3.15 g in 30 mL of distilled water) was added slowly to the reaction mixture until reaction mixture remains slightly acidic. Potassium bicarbonate was added portion wise as a solid until CO$_2$ evolution ceased, and the reaction mixture had a pH greater than 7. Water was removed under vacuo to afford a white solid. A fine powder of this solid was made by grinding using mortar and pestle and the material was dried with a gentle heating of the flask with the heat gun. The powder was transferred in to a 300 mL of boiling acetonitrile and filtered while hot. The filtrate was removed under vacuo to afford pure product as a white powder (0.91 g, 53% yield). Analytically pure sample was obtained by recrystallization from 2:1 mixture of ethanol/2-propanol. $^{19}$F NMR (376.3 MHz, D$_2$O): δ-76.7 (q, J=33.6 Hz, CF$_3$), −155.0 (q, J=40.7 Hz, 3F); $^{11}$B NMR (128.3 MHz, D$_2$O): δ 0.8 (qq, J=40.7, 33.6, 1B)

Example 23

Potassium (trifluoromethyl)trifluoroborate (K[CF$_3$—BF$_3$]) from Tri(n-butyl)borate [B(OCH$_2$CH$_2$CH$_2$CH$_3$)$_3$]

In a 10-15 mL vial with magnetic stirrer under argon was added 10 ml of dry THF. The vial was cooled to 0 to −5° C. for 5 minutes. After ten minutes, CF$_3$H was bubbled into this THF solution for 2 min (0.304 g, 4.34 mmol was added total at the rate of 52.5 ml/min). This reaction mixture was allowed to stir for ten minutes. After 10 minutes, trimethoxyborane (1 g, 4.34 mmol, 1.17 mL) was added to the reaction mixture neat. The resulting reaction mixture was stirred at 0° C. for 5 minutes. After 5 minutes, a solution of potassium hexamethyldisilazide (KHMDS) in THF (0.866 g, 4.34 mmol, 1 eq) was added to the reaction mixture drop wise and the resulting yellowish reaction mixture was stirred at 0° C. for 1-2 hrs and then the reaction mixture was allowed to warm to room temperature slowly overnight for 16 h. After 16 hours, 30 ml of water was added to the reaction mixture and the reaction mixture was stirred for 15 minutes. Reaction mixture was concentrated under vacuo to remove volatiles. Reaction mixture was further concentrated to half of its original volume under vacuo to remove water. Crude product obtained was transferred to a polyethylene (NALGENE®) bottle. This bottle was cooled in ice and then 48% aqueous solution of hydrogen fluoride (6 mL) was added to it. The resulting solution was stirred at ambient temperature for 12-14 hours. After that, a solution of potassium hydroxide (3.15 g in 30 mL of distilled water) was added slowly to the reaction mixture until reaction mixture remains slightly acidic. Potassium bicarbonate was added portion wise as a solid until CO$_2$ evolution ceased, and the reaction mixture had a pH greater than 7. Water was removed under vacuo to afford white solid. A fine powder of this solid was made by grinding using mortar and pestle and the material was dried with a gentle heating of the flask with the heat gun. The powder was transferred in to a 300 mL of boiling acetonitrile and filtered while hot. The filtrate was removed under vacuo to afford pure product as a white powder (0.51 g, 66% yield). Analytically pure sample was obtained by recrystallization from 2:1 mixture of ethanol/2-propanol. $^{19}$F NMR (376.3 MHz, D$_2$O): δ-76.7 (q, J=33.6 Hz, CF$_3$), −155.0 (q, J=40.7 Hz, 3F); $^{11}$B NMR (128.3 MHz, D$_2$O): δ 0.8 (qq, J=40.7, 33.6, 1B).

General Procedure for the trifluoromethylation of Elemental Sulfur

Example 24

To a 50 ml round bottom flask with stirrer under argon was added elemental sulfur (0.45 g, 14.2 mmol, 2 eq) followed by 10 ml of dry THF. This reaction flask was flushed with argon and it was cooled to −78° C. using dry ice/acetone and was stirred at that temperature. CF$_3$H was bubbled into this THF solution for 3 min 30 sec (0.5 g, 7.14 mmol was added total at the rate of 52.5 ml/min). This reaction mixture was allowed to stir for few minutes. A solution of potassium hexamethyldisilazide in THF (2.84 g in 5 ml, 14.2 mmol) was added drop wise to the reaction mixture and the resulting yellowish reaction mixture was stirred at −78° C. for 1 hour and then was gradually warmed to room temperature and stirred at room temperature for 10 hours. Reaction mixture was reduced to half of its original volume under vacuo and then transferred to the reparatory funnel and was extracted with pentane. Organic layer was washed with water (25 ml×2) followed by brine (25 ml×2) and then it was dried over sodium sulfate. Pentane was removed under vacuum to obtain crude product. This crude product was put in the 50 ml round bottom flask and it was oxidized with 6 eq of 30% aq H$_2$O$_2$ and 1 eq of H$_2$SO$_4$ and allowed to stir at room temperature for 1 h. After 1 h, $^{19}$F NMR was recorded which showed complete conversion of the crude product to trifluoromethanesulfonic acid ($^{19}$F NMR at −78 ppm as the only peak in the spectrum).

Accordingly, the invention demonstrates the use of a trifluoromethylating agent for trifluoromethylating a fluoromethylatable substrate in the presence of an alkoxide (polyalkoxide) or metal salt of silazane (polysilazane) under conditions sufficient to trifluoromethylate the substrate; wherein the fluoromethylatable substrate preferably comprises a compound selected from the group consisting of aldehydes, ketones, chalcones, esters, alkyl halides, alkyl formates, aryl halides, alkyl borates and sulfur.

What is claimed is:

1. A method for directly preparing a trifluoromethylated product, which comprises reacting a fluoromethylatable substrate with a trifluoromethylating agent of trifluoromethane in the presence of a base under conditions sufficient to trifluoromethylate the substrate; wherein the fluoromethylatable substrate comprises a compound selected from the group consisting of halosilanes, carbonyl compounds, alkyl formates, alkyl halides, aryl halides, alkyl borates, carbon dioxide and elemental sulfur and the reaction is a single step reaction carried out in the presence of a solvent of dimethyl ether, diethyl ether, a polyether, a hydrocarbon, dimethoxymethane, N-methylpyrrolidone, hexamethyl phosphoric triamide, or dimethyl sulfoxide.

2. The method of claim 1, wherein the fluoromethylatable substrate is a halosilane.

3. The method of claim 1, wherein the substrate comprises chlorotrimethylsilane, chlorotriethylsilane, chlorotriisopropylsilane, chloro(t-butyldimethyl)silane, chloro(tris(trimethylsilyl)) silane, dichlorodiethylsilane, benzaldehyde, p-anisaldehyde, 3-methylbenzaldehyde, 1-anthracenaldehyde, furan-2-carboxaldehyde, benzophenone, 4-methoxybenzophenone, 4-methylbenzophenone, 3-nitrobenzophenone, 4-fluorobenzophenone, chalcone, 4'-methoxychalcone, 4'-nitrochalcone, 4,4'-difluorochalcone, 4'-chlorochalcone, methyl benzoate, benzyl bromide, iodobenzene, 1-iodonaphthalene, 2-iodoanisole, 3-nitroiodobenzene, 2-iodotoluene, 3-iodo-2-methoxynitrobenzene, 3-iodobenzotrifluoride, 2-iodopyridine, 3-iodopyridine, trimethoxyborate, tributylborate, elemental sulfur, methyl formate, or ethyl formate.

4. The method of claim 1, wherein the ketone or carbonyl compound is a non-enolizable compound.

5. The method of claim 1, wherein the base comprises an alkoxide, polyalkoxide or alkali metal salt of silazane, polysilazanes or a combination thereof.

6. The method of claim 1, wherein the reaction conditions include a temperature of between about −90° C. to about 130° C. for a time between 30 minutes to 24 hours.

7. The method of claim 1, wherein the fluoromethylatable substrate comprises chlorosilanes, aldehydes, methyl benzoate, chalcones or non-enolizable ketones, the base comprises an alkoxide (polyalkoxide) or alkali metal salt of silazane, polysilazanes or a combination thereof, and the method further comprises adding the base to a mixture that includes the substrate and the trifluoromethylating agent to form a reaction mixture, stifling the reaction mixture at about −80° C. to −70° C. and warming the reaction mixture to about room temperature to trifluoromethylate the substrate.

8. The method of claim 7, wherein the reaction mixture is warmed to about room temperature for about 2 to 20 hours.

9. The method of claim 1, wherein the fluoromethylatable substrate comprises halosilane, the base comprises an alkoxide, polyalkoxide or alkali metal salt of silazane, polysilazanes or a combination thereof, and the method further comprises adding either trifluoromethylating agent to a mixture of halosilane and base or adding base to a mixture of trifluoromethylating agent and silyl halide or a combination thereof to form a reaction mixture, stifling the reaction mixture at −85° C. to room temperature to trifluoromethylate the substrate.

10. The method of claim 1, wherein the fluoromethylatable substrate comprises substrate containing carbonyl group, the base comprises an alkoxide, polyalkoxide or alkali metal salt of silazane, polysilazanes or a combination thereof, and the method further comprises adding either trifluoromethylating agent to a mixture of substrate containing carbonyl group and base or adding base to a mixture of trifluoromethylating agent and substrate containing carbonyl group or a combination thereof to form a reaction mixture, stifling the reaction mixture at −50° C. to room temperature to trifluoromethylate the substrate.

11. The method of claim 1, wherein the fluoromethylatable substrate comprises aryl halides, the base comprises an alkoxide (polyalkoxide) or alkali metal salt of silazane, polysilazanes or a combination thereof, and one of the method further comprises adding the trifluoromethylating agent to a mixture of a copper halide, a heterocyclic ligand containing 1-10 heteroatoms, the solvent and the aryl halide followed by addition of the base to form a reaction mixture, stifling the reaction mixture at about 80 to 120° C. and cooling the reaction mixture to about room temperature to trifluoromethylate the substrate and the other method further comprises adding the trifluoromethylating agent to a mixture of a copper halide and base followed by an additive and aryl halide to form a reaction mixture, stifling the reaction mixture at about 50° C. and cooling the reaction mixture to about room temperature to trifluoromethylate the substrate.

12. The method of claim 1, wherein the fluoromethylatable substrate comprises trialkylborates which are in situ converted to trifluoromethyltrifluoroborates.

13. The method of claim 1, wherein the fluoromethylatable substrate comprises a substrate containing trialkyl borate group, the base comprises an alkoxide, polyalkoxide or alkali metal salt of silazane, polysilazanes or a combination thereof, and the method further comprises adding base to a mixture of trifluoromethylating agent and substrate containing trialkyl borate group or a combination thereof to form a reaction mixture, stirring the reaction mixture at −5° C. to room temperature to trifluoromethylate the substrate followed by addition of fluorinating agent and stirring the reaction mixture at room temperature for 12-24 hours.

14. The method of claim 1, wherein the fluoromethylatable substrate is elemental sulfur which is trifluoromethylated to a trifluoromethylated sulfur intermediate, which is then oxidized in situ to trifluoromethanesulfonic acid.

15. The method of claim 1, wherein the fluoromethylatable substrate comprises a substrate containing a sulfur atom, the base comprises an alkoxide, polyalkoxide or alkali metal salt of silazane, polysilazanes or a combination thereof, and the method further comprises adding base to a mixture of trifluoromethylating agent and substrate containing elemental sulfur to form a reaction mixture, stifling the reaction mixture at −78° C. to room temperature to trifluoromethylate the substrate followed by addition of oxidizing agent, acid and stirring the reaction mixture at room temperature for 12-24 hours.

16. The method of claim 15, wherein the reaction mixture is stirred vigorously either by magnetic stirring or mechanical stifling methods at all times.

17. The method of claim 1, wherein the trifluoromethylated substrate is trifluoromethyl(trimethyl)silane, trifluoromethyl(triethyl)silane, trifluoromethyl(triisopropyl)silane, (trifluoromethyl)t-butyldimethylsilane, tris(trimethylsilyl)trifluoromethylsilane, diethyl bis(trifluoromethyl)silane, 2,2,2-trifluoro-1-phenylethanol, 2,2,2-trifluoro-1-(4-methoxyphenyl)ethanol, 2,2,2-trifluoro-1-m-tolyletahnol, 2,2,2-trifluoro-1-(furan-2-yl)ethanol, 1-(anthracen-9-yl)-2,2,2-trifluoroethanol, 2,2,2-trifluoro-1,1-diphenylethanol, 2,2,2-trifluoro-1-(4-methoxyphenyl)-1-phenylethanol, 2,2,2-trifluoro-1-phenyl-1-p-tolylethanol, 2,2,2-trifluoro-1-(3-nitrophenyl)-1-phenylethanol, 2,2,2-trifluoro-1-(4-fluorophenyl)-1-phenylethanol, (E)-1,1,1-trifluoro-2,4-diphenylbut-3-en-2-ol, (E)-1,1,1-trifluoro-2-(4-methoxyphenyl)-4-phenylbut-3-en-2-ol, (E)-1,1,1-trifluoro-2-(4-nitrophenyl)-4-phenylbut-3-en-2-ol, (E)-1,1,1-trifluoro-2,4-bis(4-fluorophenyl)but-3-en-2-ol, (E)-2-(4-chlorophenyl)-1,1,1-trifluoro-4-phenylbut-3-en-2-ol, 2,2,2-trifluoro-1-phenylethanone, 2,2,2-trifluoroethyl)benzene, (trifluoromethyl)benzene, 1-trifluoromethylnaphthalene, 1-methoxy-2-(trifluoromethyl)benzene, 1-nitro-3-(trifluoromethyl)benzene, 1-methyl-2-(trifluoromethyl)benzene, 2-methoxy-1-nitro-3-(trifluoromethyl)benzene, 1,3-bis(trifluoromethyl)benzene, 2-(trifluoromethyl)pyridine, 3-(trifluoromethyl)pyridine, potassium (trifluoromethyl)trifluoroborate, trifluoromethanesulfonic acid, 1-methoxy-2,2,2-trifluoroethanol, or 1-ethoxy-2,2,2-trifluoroethanol.

18. The method of claim 1, wherein the trifluoromethylatable substrate includes a chlorosilane or chloroalkyl silane.

19. The method of claim 18 wherein the base trifluoromethylating agent and substrate are combined to form a reaction mixture, and the method further comprises stifling the reaction mixture at a temperature of between −50° C. to room temperature to trifluoromethylate the substrate.

20. The method of claim 19, wherein the reaction mixture is stirred vigorously either by magnetic stifling or mechanical stirring methods at all times.

21. The method of claim 20, wherein the base comprises an alkoxide, polyalkoxide or alkali metal salt of silazane, polysilazanes or a combination thereof.

* * * * *

UNITED STATES PATENT AND TRADEMARK OFFICE
CERTIFICATE OF CORRECTION

PATENT NO.          : 9,334,253 B2                                          Page 1 of 1
APPLICATION NO.     : 14/113482
DATED               : May 10, 2016
INVENTOR(S)         : Prakash et al.

It is certified that error appears in the above-identified patent and that said Letters Patent is hereby corrected as shown below:

On the Title Page:
Item (57) ABSTRACT, line 5, before "agent in the presence of an alkoxide or", change "trifiuoromethylating" to -- trifluoromethylating --.

In the Claims:
Column 32:
Line 63 (claim 7, line 8), before "the reaction mixture at about -80°", change "stifling" to -- stirring --.

Column 33:
Line 8 (claim 9, line 8), before "the reaction mixture at -85°", change "stifling" to -- stirring --.
Line 18 (claim 10, line 9), before "the reaction mix-", change "stifling" to -- stirring --.
Line 28 (claim 11, line 8), after "addition of the base to form a reaction mixture,", change "stifling" to -- stirring --.
Line 34 (claim 11, line 14), before "the reaction mixture at about", change "stifling" to -- stirring --.

Column 34:
Line 7 (claim 15, line 7), before "the reaction mixture at", change "stifling" to -- stirring --.
Line 13 (claim 16, line 3), before "methods at all times.", change "stifling" to -- stirring --.
Line 45 (claim 19, line 3), after "tion mixture, and the method further comprises", change "stifling" to -- stirring --.
Line 49 (claim 20, line 2), before "or mechanical", change "stifling" to -- stirring --.

Signed and Sealed this
Twenty-first Day of June, 2016

Michelle K. Lee
*Director of the United States Patent and Trademark Office*